United States Patent
Bonfanti et al.

(10) Patent No.: US 8,034,835 B2
(45) Date of Patent: Oct. 11, 2011

(54) 1-[[2-AMINO-3-(SUBSTITUTED ALKYL)-3H-BENZIMIDAZOLYL[METHYL]-3-SUBSTITUTED-1,3-DIHYDRO-BENZOIMIDAZOL-2-ONES AND STRUCTURAL ANALOGS

(75) Inventors: Jean-François Bonfanti, Andé (FR); Philippe Muller, Andé (FR); Jérôme Michel Claude Fortin, Igoville (FR); Frédéric Marc Maurice Doublet, Isneauville (FR)

(73) Assignee: Tibotec Pharmaceuticals Ltd. (IE)

( * ) Notice: Subject to any disclaimer, the term of this patent is extended or adjusted under 35 U.S.C. 154(b) by 899 days.

(21) Appl. No.: 11/993,109

(22) PCT Filed: Jun. 20, 2006

(86) PCT No.: PCT/EP2006/063365
§ 371 (c)(1), (2), (4) Date: Dec. 19, 2007

(87) PCT Pub. No.: WO2006/136561
PCT Pub. Date: Dec. 28, 2006

(65) Prior Publication Data
US 2010/0183552 A1   Jul. 22, 2010

(30) Foreign Application Priority Data
Jun. 20, 2005   (EP) .................... 05076438

(51) Int. Cl.
*C07D 235/04* (2006.01)
*C07D 403/02* (2006.01)
*A01N 43/52* (2006.01)
*A61K 31/415* (2006.01)

(52) U.S. Cl. .................... 514/394; 548/305.4

(58) Field of Classification Search ............... 548/305.4; 514/394
See application file for complete search history.

(56) References Cited

FOREIGN PATENT DOCUMENTS

| WO | WO 01/00611 A1 | 1/2001 |
|---|---|---|
| WO | WO 01/00612 A2 | 1/2001 |
| WO | WO 01/00615 A1 | 1/2001 |
| WO | WO 01/95910 A1 | 12/2001 |
| WO | WO 2005/058869 | 6/2005 |

OTHER PUBLICATIONS

Patani et al. Chem. Rev. (1996), vol. 96, pp. 3147-3176.*

* cited by examiner

*Primary Examiner* — D M Seaman
*Assistant Examiner* — Niloofar Rahmani
(74) *Attorney, Agent, or Firm* — Mary A. Appollina

(57) ABSTRACT

Inhibitors of RSV replication of formula (I) which can be represented by formula (I)

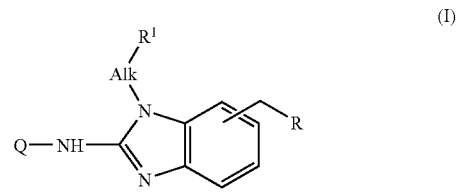

the salts and stereochemically isomeric forms thereof, wherein
R is a radical of formula

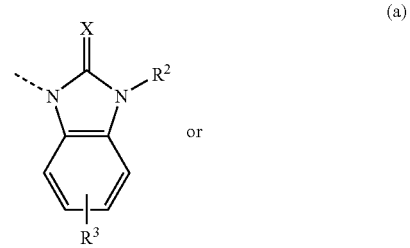

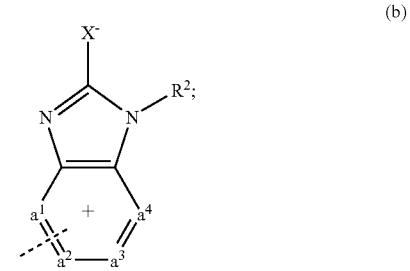

Q is hydrogen or $C_{1-6}$alkyl optionally substituted with a heterocycle or Q is $C_{1-6}$alkyl substituted with both a radical —$OR^4$ and a heterocycle; Alk is $C_{1-6}$alkanediyl; X is O or S; -$a^1$=$a^2$-$a^3$=$a^4$- is —N=CH—CH=CH—, —CH=N—CH=CH—, —CH=CH—N=CH— or —CH=CH—CH=N—; $R^1$ is Ar or a heterocycle; $R^2$ is hydrogen, $C_{1-6}$alkyl, substituted $C_{1-6}$alkyl, $C_{3-7}$cycloalkyl; $R^3$ is hydrogen, $C_{1-6}$alkyl, cyano, aminocarbonyl, polyhalo$C_{1-6}$alkyl, $C_{2-6}$alkenyl or $C_{2-6}$alkynyl;
$R^4$ is hydrogen or $C_{1-6}$alkyl; Ar is phenyl or substituted phenyl; Het is a heterocycle; pharmaceutical compositions containing compounds (I) and processes for preparing compounds (I).

13 Claims, No Drawings

1-[[2-AMINO-3-(SUBSTITUTED ALKYL)-3H-BENZIMIDAZOLYL[METHYL]-3-SUBSTITUTED-1,3-DIHYDRO-BENZOIMIDAZOL-2-ONES AND STRUCTURAL ANALOGS

This application is a National Stage application under 35 U.S.C. 371 of PCT International Application No. PCT/EP2006/063365, filed Jun. 20, 2006, which claims priority from European Patent Application No. EP 05076438.0, filed Jun. 20, 2005, the contents of which are hereby incorporated by reference.

The present invention is concerned with 1-[[2-amino-3-(substituted alkyl)-3H-benzimidazolyl]methyl]-3-subtituted-1,3-dihydro-benzoimidazol-2-ones and structural analogs having inhibitory activity on the replication of the respiratory syncytial virus (RSV). It further concerns compositions comprising these compounds as active ingredient as well as processes for preparing these compounds and compositions.

Human RSV or Respiratory Syncytial Virus is a large RNA virus, member of the family of Paramyxoviridae, subfamily pneumovirinae together with bovine RSV virus. Human RSV is responsible for a spectrum of respiratory tract diseases in people of all ages throughout the world. RSV is prevalent among children younger than two years of age and is the major cause of lower respiratory tract illness during infancy and childhood. Over half of all infants encounter RSV in their first year of life, and almost all within their first two years. The infection in young children can cause lung damage that persists for years and may contribute to chronic lung disease in later life (chronic wheezing, asthma), particularly to chronic obstructive pulmonary disorder (COPD). Older children and adults often suffer from a (bad) common cold upon RSV infection. In old age, susceptibility again increases, and RSV has been implicated in a number of outbreaks of pneumonia in the aged resulting in significant mortality. Additionally, RSV may cause serious disease in immunodeficient or in immunosuppressed persons, particularly bone marrow transplant patients.

Infection with a virus from a given subgroup does not protect against a subsequent infection with an RSV isolate from the same subgroup in the following winter season. Re-infection with RSV is thus common, despite the existence of only two subtypes, A and B.

Today only three drugs have been approved for use against RSV infection. A first one is ribavirin, a nucleoside analogue, provides an aerosol treatment for serious RSV infection in hospitalized children. The aerosol route of administration, the toxicity (risk of teratogenicity), the cost and the highly variable efficacy limit its use. The other two drugs, RespiGam® and palivizumab, polyclonal and monoclonal antibody immunostimulants, are intended to be used in a preventive way.

Other attempts to develop a safe and effective RSV vaccine have all met with failure thus far. Inactivated vaccines failed to protect against disease, and in fact in some cases enhanced disease during subsequent infection. Life attenuated vaccines have been tried with limited success. Clearly there is a need for an efficacious non-toxic and easy to administer drug against RSV replication.

A number of benzimidazole and imidazopyridine derivatives have been described in WO-01/00611, WO-01/00612 and WO-01/00615 as inhibitors of RSV replication. WO-01/95910 discloses imidazopyridines and imidazopyrimidines useful in the treatment of RSV infection. The compounds of the present invention differ from these prior art compounds both in terms of chemical structure and activity profile.

The present invention concerns inhibitors of RSV replication, which can be represented by formula (I)

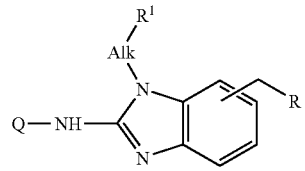

the salts and stereochemically isomeric forms thereof, wherein R is a radical of formula

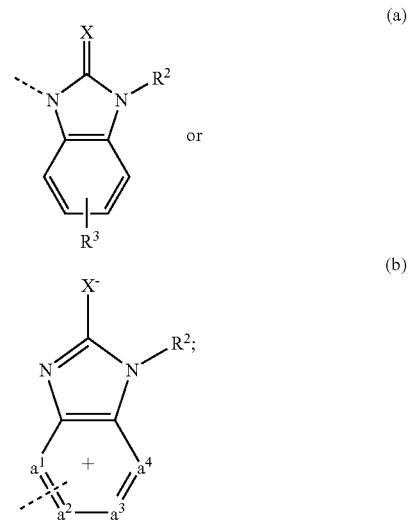

Q is hydrogen or $C_{1-6}$alkyl optionally substituted with a heterocycle or Q is $C_{1-6}$alkyl substituted with both a radical —$OR^4$ and a heterocycle; wherein said heterocycle is selected from the group consisting of oxazolidine, thiazolidine, 1-oxo-thiazolidine, 1,1-dioxothiazolidine, morpholinyl, thiomorpholinyl, 1-oxo-thiomorpholinyl, 1,1-dioxothiomorpholinyl, hexahydrooxazepine, hexahydrothiazepine, 1-oxo-hexahydrothiazepine, 1,1-dioxo-hexahydrothiazepine, pyrrolidine, piperidine, homopiperidine, piperazine; wherein each of said heterocycle may be optionally substituted with one or two substituents selected from the group consisting of $C_{1-6}$alkyl, hydroxy$C_{1-6}$alkyl, aminocarbonyl$C_{1-6}$alkyl, hydroxy, carboxyl, $C_{1-6}$alkyloxycarbonyl, aminocarbonyl, mono- or di($C_{1-6}$alkyl)aminocarbonyl, $C_{1-6}$alkylcarbonylamino, aminosulfonyl and mono- or di($C_{1-6}$alkyl)aminosulfonyl;

Alk is $C_{1-6}$alkanediyl;

X is O or S;

-$a^1$=$a^2$-$a^3$=$a^4$- is a bivalent radical of formula —N═CH—CH═CH—, —CH═N—CH═CH—, —CH═CH—N═CH— or —CH═CH—CH═N—; wherein one of the nitrogen atoms bears the chemical bond linking radical (b) with the rest of the molecule;

$R^1$ is Ar or a heterocycle selected from pyridyl, pyrazinyl, pyridazinyl, pyrimidinyl, furanyl, tetrahydrofuranyl, thienyl, pyrrolyl, thiazolyl, oxazolyl, imidazolyl, isothiazolyl, pyrazolyl, isoxazolyl, oxadiazolyl, quinolinyl, quinoxalinyl, benzofuranyl, benzothienyl, benzimidazolyl, benzoxazolyl, benzothiazolyl, pyridopyridyl, naphthiridinyl, 1H-imidazo[4,5-b]pyridinyl, 3H-imidazo[4,5-b]-pyridinyl, imidazo[1,2-a]pyridinyl and 2,3-dihydro-1,4-dioxino [2,3-b]pyridyl; wherein each of said heterocycle may optionally be substituted with 1, 2, or 3 substituents each independently selected from the group consisting of halo, hydroxy, amino, cyano, carboxyl, $C_{1-6}$alkyl, $C_{1-6}$alkyloxy, hydroxy$C_{1-6}$alkyloxy, ($C_{1-6}$alkyl-oxy)$C_{1-6}$alkyloxy, $C_{1-6}$alkylthio, $C_{1-6}$alkyloxy$C_{1-6}$alkyl, hydroxy$C_{1-6}$alkyl, mono- or di($C_{1-6}$alkyl)amino, mono- or di($C_{1-6}$alkyl)amino$C_{1-6}$alkyl, polyhalo$C_{1-6}$alkyl, $C_{1-6}$alkylcarbonylamino, $C_{1-6}$alkyloxycarbonyl, aminocarbonyl, mono- and di-$C_{1-6}$ alkylaminocarbonyl;

$R^2$ is hydrogen, $C_{1-6}$alkyl, hydroxy$C_{1-6}$alkyl, $C_{1-6}$alkyloxy$C_{1-6}$alkyl, Ar—$C_{1-6}$alkyloxy-$C_{1-6}$alkyl, $C_{3-7}$cycloalkyl, cyano-$C_{1-6}$alkyl, Ar—$C_{1-6}$alkyl, Het-$C_{1-6}$alkyl;

$R^3$ is hydrogen, $C_{1-6}$alkyl, cyano, aminocarbonyl, polyhalo$C_{1-6}$alkyl, $C_{2-6}$alkenyl or $C_{2-6}$alkynyl;

$R^4$ is hydrogen or $C_{1-6}$alkyl;

each Ar independently is phenyl or phenyl substituted with 1 to 5, such as 1, 2, 3 or 4, substituents selected from halo, hydroxy, amino, mono- or di($C_{1-6}$alkyl)amino, $C_{1-6}$alkylcarbonylamino, $C_{1-6}$alkylsulfonylamino, cyano, $C_{1-6}$alkyl, $C_{2-6}$alkenyl, $C_{2-6}$alkynyl, phenyl, hydroxy$C_{1-6}$alkyl, polyhalo$C_{1-6}$alkyl, amino$C_{1-6}$alkyl, mono- or di($C_{1-6}$alkyl) amino$C_{1-6}$alkyl, $C_{1-6}$alkyloxy, polyhalo$C_{1-6}$alkyloxy, phenoxy, aminocarbonyl, mono- or di($C_{1-6}$alkyl) aminocarbonyl, hydroxycarbonyl, $C_{1-6}$alkoxycarbonyl, $C_{1-6}$alkylcarbonyl, aminosulfonyl, mono- and di($C_{1-6}$ alkyl)-aminosulfonyl;

Het is a heterocycle selected from the group consisting of pyridyl, pyrazinyl, pyridazinyl, pyrimidinyl, furanyl, tetrahydrofuranyl, thienyl, pyrrolyl, thiazolyl, oxazolyl, imidazolyl, isothiazolyl, pyrazolyl, isoxazolyl, oxadiazolyl, quinolinyl, quinoxalinyl, benzofuranyl, benzothienyl, benzimidazolyl, benzoxazolyl, benzothiazolyl, pyridopyridyl, naphthiridinyl, 1H-imidazo[4,5-b]pyridinyl, 3H-imidazo [4,5-b]pyridinyl, imidazo[1,2-a]pyridinyl and 2,3-dihydro-1,4-dioxino-[2,3-b]pyridyl; wherein each Het may be optionally substituted with 1, 2 or 3 substituents each independently selected from halo, hydroxy, amino, mono- or di($C_{1-6}$alkyl)amino, cyano, $C_{1-6}$alkyl, hydroxy$C_{1-6}$alkyl, polyhalo$C_{1-6}$alkyl, $C_{1-6}$alkyloxy.

The dotted line in radicals (a) and (b) represents the bond linking (a) or (b) to the rest of the molecule. In radical (b) this bond is to one of the nitrogen atoms in $a^1=a^2-a^3=a^4$ which thereby is positively charged (pyridinium cation).

The invention also relates to the use of a compound of formula (I), or an addition salt, or stereochemically isomeric form thereof, for the manufacture of a medicament for inhibiting RSV replication. Or the invention relates to a method of inhibiting RSV replication in a warm-blooded animal said method comprising the administration of an effective amount of a compound of formula (I), an addition salt, or stereochemically isomeric form thereof.

As used in the foregoing and hereinafter, 'polyhalo$C_{1-6}$ alkyl' as a group or part of a group, e.g. in polyhalo$C_{1-6}$ alkyloxy, is defined as mono- or polyhalo substituted $C_{1-6}$alkyl, in particular $C_{1-6}$alkyl substituted with up to one, two, three, four, five, six, or more halo atoms, such as methyl or ethyl with one or more fluoro atoms, for example, difluoromethyl, trifluoromethyl, trifluoroethyl. Preferred is trifluoromethyl. Also included are perfluoro $C_{1-6}$alkyl groups, which are $C_{1-6}$alkyl groups wherein all hydrogen atoms are replaced by fluoro atoms, e.g. pentafluoroethyl. In case more than one halogen atom is attached to an alkyl group within the definition of polyhalo-$C_{1-4}$alkyl, the halogen atoms may be the same or different.

Each Ar may be unsubstituted phenyl or phenyl substituted with 1 to 5 substituents, such as 5 or 4 substituents or, which is preferred, up to 3 substituents, or up to two substituents, or with one substituent.

A hydroxy$C_{1-6}$alkyl group when substituted on an oxygen atom or a nitrogen atom preferably is a hydroxy$C_{2-6}$alkyl group wherein the hydroxy group and the oxygen or nitrogen are separated by at least two carbon atoms.

As used herein "$C_{1-4}$alkyl" as a group or part of a group defines straight or branched chain saturated hydrocarbon radicals having from 1 to 4 carbon atoms such as for example methyl, ethyl, 1-propyl, 2-propyl, 1-butyl, 2-butyl, 2-methyl-1-propyl; "$C_{1-6}$alkyl" encompasses $C_{1-4}$alkyl radicals and the higher homologues thereof having 5 or 6 carbon atoms such as, for example, 1-pentyl, 2-pentyl, 3-pentyl, 1-hexyl, 2-hexyl, 2-methyl-1-butyl, 2-methyl-1-pentyl, 2-ethyl-1-butyl, 3-methyl-2-pentyl, and the like. Of interest amongst $C_{1-6}$alkyl is $C_{1-4}$alkyl.

The term "$C_{2-6}$alkenyl" as a group or part of a group defines straight and branched chained hydrocarbon radicals having saturated carbon-carbon bonds and at least one double bond, and having from 2 to 6 carbon atoms, such as, for example, ethenyl (or vinyl), 1-propenyl, 2-propenyl (or allyl), 1-butenyl, 2-butenyl, 3-butenyl, 2-methyl-2-propenyl, 2-pentenyl, 3-pentenyl, 2-hexenyl, 3-hexenyl, 4-hexenyl, 2-methyl-2-butenyl, 2-methyl-2-pentenyl and the like. Of interest amongst $C_{2-6}$alkenyl is $C_{2-4}$alkenyl.

The term "$C_{2-6}$alkynyl" as a group or part of a group defines straight and branched chained hydrocarbon radicals having saturated carbon-carbon bonds and at least one triple bond, and having from 2 to 6 carbon atoms, such as, for example, ethynyl, 1-propynyl, 2-propynyl, 1-butynyl, 2-butynyl, 3-butynyl, 2-pentynyl, 3-pentynyl, 2-hexynyl, 3-hexynyl and the like. Of interest amongst $C_{2-6}$alkynyl is $C_{2-4}$alkynyl.

$C_{3-7}$cycloalkyl is generic to cyclopropyl, cyclobutyl, cyclopentyl, cyclohexyl and cycloheptyl.

$C_{1-6}$alkanediyl defines bivalent straight and branched chain saturated hydrocarbon radicals having from 1 to 6 carbon atoms such as, for example, methylene, ethylene, 1,3-propanediyl, 1,4-butanediyl, 1,2-propanediyl, 2,3-butanediyl, 1,5-pentanediyl, 1,6-hexanediyl and the like. Of interest amongst $C_{1-6}$alkanediyl is $C_{1-4}$alkanediyl.

As used herein before, the term (=O) forms a carbonyl moiety when attached to a carbon atom, a sulfoxide moiety when attached to a sulfur atom and a sulfonyl moiety when two of said terms are attached to a sulfur atom.

The term halo is generic to fluoro, chloro, bromo and iodo.

It should be noted that the radical positions on any molecular moiety used in the definitions may be anywhere on such moiety as long as it is chemically stable.

Radicals used in the definitions of the variables include all possible isomers unless otherwise indicated. For instance pyridyl includes 2-pyridyl, 3-pyridyl and 4-pyridyl; pentyl includes 1-pentyl, 2-pentyl and 3-pentyl.

When any variable occurs more than one time in any constituent, each definition is independent.

Some of the compounds of formula (I) may contain one or more centers of chirality and exist as stereochemically isomeric forms. The term "stereochemically isomeric forms" as used herein defines all the possible compounds made up of the same atoms bonded by the same sequence of bonds but having different three-dimensional structures which are not interchangeable, which the compounds of formula (I) may possess.

Unless otherwise mentioned or indicated, the chemical designation of a compound encompasses the mixture of all possible stereochemically isomeric forms, which said compound may possess. Said mixture may contain all diastereomers and/or enantio-mers of the basic molecular structure of said compound. All stereochemically isomeric forms of the compounds of the present invention both in pure form or mixed with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyl-tartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of formula (I) can be obtained separately by conventional methods. Appropriate physical separation methods that may advantageously be employed are, for example, selective crystallization and chromatography, e.g. column chromatography.

For some of the compounds of formula (I) and the intermediates used in the preparation thereof, the absolute stereochemical configuration was not experimentally determined. A person skilled in the art is able to determine the absolute configuration of such compounds using art-known methods such as, for example, X-ray diffraction.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

The term "compounds of formula (I)", or any similar terms such as "compounds of the invention" and the like, is meant to also comprise any prodrugs that the compounds of formula (I) may form. The term "prodrug" as used herein is meant to comprise any pharmacologically acceptable derivatives such as esters, amides and phosphates, such that the resulting in vivo biotransformation product of the derivative is the active drug as defined in the compounds of formula (I). The reference by Goodman and Gilman (The Pharmacological Basis of Therapeutics, 8$^{th}$ ed, McGraw-Hill, Int. Ed. 1992, "Biotransformation of Drugs", p 13-15) describing prodrugs generally is hereby incorporated. Prodrugs preferably have excellent aqueous solubility, increased bioavailability and are readily metabolized into the active inhibitors in vivo. Prodrugs of a compound of the present invention may be prepared by modifying functional groups present in the compound in such a way that the modifications are cleaved, either by routine manipulation or in vivo, to the parent compound.

Preferred are pharmaceutically acceptable ester prodrugs that are hydrolysable in vivo and are derived from those compounds of formula (I) having a hydroxy or a carboxyl group. An in vivo hydrolysable ester is an ester, which is hydrolysed in the human or animal body to produce the parent acid or alcohol. Suitable pharmaceutically acceptable esters for carboxy include $C_{1-6}$alkoxymethyl esters for example methoxy-methyl, $C_{1-6}$alkanoyloxymethyl esters for example pivaloyloxymethyl, phthalidyl esters, $C_{3-7}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onyl-methyl; and $C_{1-6}$alkoxycarbonyloxyethyl esters for example 1-methoxycarbonyl-oxyethyl which may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxy-methoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring. Alkanoyl esters for example are any $C_{1-30}$alkanoyl esters, in particular $C_{8-30}$alkanoyl esters, more in particular $C_{10-24}$alkanoyl esters, further in particular $C_{16-20}$alkanoyl esters, wherein the alkyl part may have one or more double bonds. Examples of alkanoyl esters are decanoate, palmitate and stearate.

The term "compounds of formula (I)", or any similar terms such as "compounds of the invention" and the like, is meant to also comprise any metabolites that are formed in vivo upon administration of the drug. Some examples of metabolites in accordance with the invention include, but are not limited to, (a) where the compound of formula (I) contains a methyl group, a hydroxymethyl derivative thereof; (b) where the compound of formula (I) contains an alkoxy group, an hydroxy derivative thereof; (c) where the compound of formula (I) contains a tertiary amino group, a secondary amino derivative thereof; (d) where the compound of formula (I) contains a secondary amino group, a primary derivative thereof; (e) where the compound of formula (I) contains a phenyl moiety, a phenol derivative thereof; and (f) where the compound of formula (I) contains an amide group, a carboxylic acid derivative thereof.

The term "compounds of formula (I)", or any similar terms such as "compounds of the invention" and the like, is meant to also comprise any N-oxide forms of the compounds of formula (I), which are compounds of formula (I) wherein one or several nitrogen atoms are oxidized to the N-oxide form.

The term "compounds of formula (I)", or any similar terms such as "compounds of the invention" and the like, is meant to also comprise quaternary amines which are the quaternary ammonium salts which the compounds of formula (I) are able to form by reaction between a basic nitrogen of a compound of formula (I) and an appropriate quaternizing agent, such as, for example, an optionally substituted alkyl halide, aryl halide or arylalkyl halide, e.g. methyl iodide or benzyl iodide. Other reactants with good leaving groups may also be used, such as alkyl trifluoromethanesulfonates, alkyl methanesulfonates, and alkyl p-toluenesulfonates. A quaternary amine has a positive charged nitrogen. Pharmaceutically acceptable counter ions include chloro, bromo, iodo, trifluoroacetate and acetate. The counter ion of choice can be introduced using ion exchange resins.

The term "compounds of formula (I)", or any similar terms such as "compounds of the invention" and the like, is meant to also comprise the metal complexes or metal chelates thereof wherein the complex or chelate is derived from physiologically acceptable metal ions such as Ca, Zn, Mg or Fe ions. Such metal complex or chelate derivatives of the compounds of formula (I) can be obtained by reacting a compound of formula (I) with a metal salt.

For therapeutic use, salts of the compounds of formula (I) are those wherein the counter-ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butane-dioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates which the compounds of formula (I) as well as the salts thereof, are able to form. Such solvates are for example hydrates, alcoholates and the like.

Some of the compounds of formula (I) may also exist in their tautomeric form. Such forms although not explicitly indicated in the above formula are intended to be included within the scope of the present invention.

Embodiments of the present invention concern compounds of formula (I-a) or (I-b):

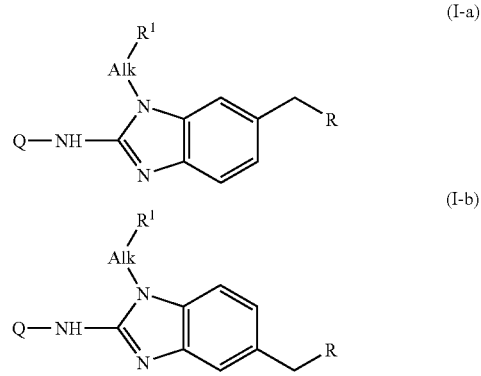

Further embodiments concern compounds of formula (I-a-1) or (I-a-2):

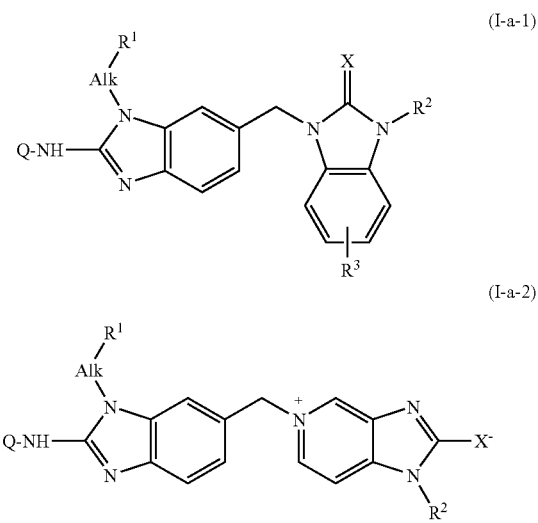

In (I-a), (I-b), (I-a-1) and (I-a-2) Q, R, Alk, X, $R^1$, $R^2$, $R^3$ are as specified in the definitions of the compounds of formula (I) or of any of the subgroups of compounds of formula (I) specified herein.

It is to be understood that the above defined subgroups of compounds of formulae (I-a), (I-b), (I-a-1) or (I-a-2), as well as any other subgroup defined herein, are meant to also comprise any addition salts and stereochemically isomeric forms of such compounds.

A number of subgroups of compounds of formula (I) are specified hereafter by restricted definitions of the various radicals in the compounds of formula (I). These subgroups however are also meant to comprise those with any permutation of the restricted definitions mentioned hereinafter.

Subgroups I of the compounds of formula (I) are those compounds of formula (I), or any subgroup of compounds of formula (I) specified herein, wherein Alk is ethylene or methylene, more in particular wherein Alk is methylene.

Subgroups II of the compounds of formula (I) are those compounds of formula (I), or any subgroup of compounds of formula (I) specified herein, such as the subgroups I mentioned above, wherein (a) R¹ is Ar or a heterocycle selected from pyridyl, pyrazinyl, pyridazinyl, pyrimidinyl, furanyl, thienyl, pyrrolyl, thiazolyl, oxazolyl, imidazolyl, isothiazolyl, pyrazolyl, isoxazolyl, quinolinyl, benzofuranyl, benzimidazolyl, benzoxazolyl, benzothiazolyl; wherein each of said heterocycle may optionally be substituted with 1, 2, or 3 substituents each independently selected from the group consisting of halo, hydroxy, amino, cyano, carboxyl, $C_{1-6}$alkyl, $C_{1-6}$alkyloxy, $C_{1-6}$alkyloxy$C_{1-6}$alkyl, hydroxy-$C_{1-6}$alkyl, mono- or di($C_{1-6}$alkyl)amino, mono- or di($C_{1-6}$alkyl)amino$C_{1-6}$alkyl, polyhalo$C_{1-6}$alkyl, $C_{1-6}$alkyloxycarbonyl, aminocarbonyl, mono- and di-$C_{1-6}$alkylaminocarbonyl;

(b) R¹ is Ar, or a heterocycle selected from quinolinyl, benzimidazolyl, pyrazinyl or pyridyl; wherein each of said heterocycle may optionally be substituted with 1, 2, or 3 substituents each independently selected from the group consisting of halo, hydroxy, amino, cyano, carboxyl, $C_{1-6}$alkyl, $C_{1-6}$alkyloxy, $C_{1-6}$alkyloxy$C_{1-6}$alkyl, hydroxy$C_{1-6}$alkyl, mono- or di($C_{1-6}$alkyl)amino, mono- or di($C_{1-6}$alkyl)amino-$C_{1-6}$alkyl, polyhalo$C_{1-6}$alkyl, $C_{1-6}$alkyloxycarbonyl, aminocarbonyl, mono- and di-$C_{1-6}$alkylaminocarbonyl;

(c) R¹ is Ar, quinolinyl, benzimidazolyl, pyrazinyl or pyridyl, wherein each of these radicals may optionally be substituted with one, two or three radicals selected from the group consisting of halo, hydroxy, $C_{1-6}$alkyl, $C_{1-6}$alkyloxy;

(d) R¹ is phenyl optionally substituted with one, two or three radicals selected from the group consisting of halo, hydroxy, $C_{1-6}$alkyl, $C_{1-6}$alkyloxy; quinolinyl; benzimidazolyl optionally substituted with $C_{1-6}$alkyl; pyridyl optionally substituted with one or two radicals selected from hydroxy, halo, $C_{1-6}$alkyl, benzyloxy and $C_{1-6}$alkyloxy, pyrazinyl optionally substituted with up to three radicals selected from $C_{1-6}$alkyl; or pyridyl substituted or optionally substituted as specified above in (a)-(i);

(e) R¹ is phenyl optionally substituted with one or two radicals selected from the group consisting of halo, hydroxy, $C_{1-6}$alkyl, $C_{1-6}$alkyloxy;

(f) R¹ is pyrazinyl optionally substituted with up to three radicals selected from $C_{1-6}$alkyl;

(g) R¹ is pyridyl substituted with 1 or 2 substituents independently selected from the group consisting of hydroxy, $C_{1-6}$alkyl, halo, $C_{1-6}$alkyloxy and ($C_{1-6}$alkyloxy)$C_{1-6}$alkyloxy;

(h) R¹ is pyridyl substituted with 1 or 2 substituents independently selected from the group consisting of hydroxy, $C_{1-6}$alkyl, halo and $C_{1-6}$alkyloxy;

(i) R¹ is pyridyl substituted with 1 or 2 substituents independently selected from the group consisting of hydroxy and $C_{1-6}$alkyl;

(j) R¹ is pyridyl substituted with hydroxy and $C_{1-6}$alkyl.

Embodiments of the invention are compounds of formula (I) or any of the subgroups of compounds of formula (I) wherein Alk is methylene and R¹ is as specified above in (a)-(j).

Subgroups III of the compounds of formula (I) are those compounds of formula (I), or any subgroup of compounds of formula (I) specified herein, such as the subgroups I and II mentioned above, wherein (a) R² is hydrogen, $C_{1-6}$alkyl, hydroxy$C_{1-6}$alkyl, $C_{1-6}$alkyloxy$C_{1-6}$alkyl, Ar—$C_{1-6}$alkyloxy$C_{1-6}$alkyl, $C_{3-7}$cycloalkyl, cyano-$C_{1-6}$alkyl, Ar—$C_{1-6}$alkyl;

(b) R² is $C_{1-6}$alkyl, hydroxy$C_{1-6}$alkyl, $C_{1-6}$alkyloxy$C_{1-6}$alkyl, Ar—$C_{1-6}$alkyloxy$C_{1-6}$alkyl, $C_{3-7}$cycloalkyl, cyano-$C_{1-6}$alkyl, Ar—$C_{1-6}$alkyl;

(c) R² is hydroxy$C_{1-6}$alkyl, $C_{1-6}$alkyloxy$C_{1-6}$alkyl, Ar—$C_{1-6}$alkyloxy$C_{1-6}$alkyl, $C_{3-7}$ cycloalkyl;

(d) R² is $C_{3-7}$cycloalkyl;

(e) R² is cyclopropyl.

Subgroups IV of the compounds of formula (I) are those compounds of formula (I), or any subgroup of compounds of formula (I) specified herein, such as the subgroups I, II and III mentioned above, wherein (a) Het is pyridyl, pyrazinyl, pyridazinyl, pyrimidinyl, furanyl, tetrahydrofuranyl, thienyl, pyrrolyl, thiazolyl, oxazolyl, imidazolyl, isothiazolyl, pyrazolyl, isoxazolyl, oxadiazolyl, quinolinyl, quinoxalinyl, benzofuranyl, benzothienyl, benzimidazolyl, benzoxazolyl, benzothiazolyl; wherein each Het may be optionally substituted with 1, 2 or 3 substituents each independently selected from halo, hydroxy, amino, mono- or di($C_{1-4}$alkyl)amino, cyano, $C_{1-6}$alkyl, hydroxy$C_{1-6}$alkyl, polyhalo$C_{1-6}$alkyl, $C_{1-6}$alkyloxy;

(b) Het is pyridyl, pyrazinyl, pyridazinyl, pyrimidinyl, furanyl, tetrahydrofuranyl, thienyl, pyrrolyl, thiazolyl, oxazolyl, imidazolyl, isothiazolyl, pyrazolyl, isoxazolyl, oxadiazolyl, quinolinyl, quinoxalinyl; wherein each Het may be optionally substituted with 1, 2 or 3 substituents each independently selected from halo, hydroxy, amino, mono- or di($C_{1-4}$alkyl)amino, cyano, $C_{1-6}$alkyl, hydroxy$C_{1-6}$alkyl, polyhalo$C_{1-6}$alkyl, $C_{1-6}$alkyloxy;

(c) Het is pyridyl, pyrazinyl, pyrimidinyl, furanyl, thienyl, thiazolyl, oxazolyl, imidazolyl; wherein each Het may be optionally substituted with 1, 2 or 3 substituents each independently selected from halo, hydroxy, amino, mono- or di($C_{1-4}$alkyl)amino, cyano, $C_{1-6}$alkyl, hydroxy$C_{1-6}$alkyl, polyhalo$C_{1-6}$alkyl, $C_{1-6}$alkyloxy;

(d) Het is pyridyl, pyrazinyl, pyrimidinyl, furanyl, thienyl, thiazolyl, oxazolyl, imidazolyl; wherein each Het may be optionally substituted with 1, 2 or 3 substituents each independently selected from halo, hydroxy, amino, mono- or di($C_{1-4}$alkyl)amino, cyano, $C_{1-6}$alkyl, $C_{1-6}$alkyloxy; or (e) Het is a heterocycle selected from the group consisting of pyridyl, pyrazinyl, pyrimidinyl, furanyl, thienyl, thiazolyl, oxazolyl, imidazolyl.

Subgroups V of the compounds of formula (I) are those compounds of formula (I), or any subgroup of compounds of formula (I) specified herein, such as the subgroups I, II, III and IV mentioned above, wherein (a) R³ is hydrogen, $C_{1-6}$alkyl, cyano, aminocarbonyl; or (b) R³ is hydrogen.

Subgroups VI of the compounds of formula (I) are those compounds of formula (I), or any subgroup of compounds of formula (I) specified herein, such as the subgroups I, II, III, IV and V mentioned above, wherein R⁴ is hydrogen.

Subgroups VII of the compounds of formula (I) are those compounds of formula (I), or any subgroup of compounds of formula (I) specified herein, such as the subgroups I, II, III, IV, V and VI mentioned above, wherein -a¹=a²-a³=a⁴ is a bivalent radical of formula —CH=CH—CH=CH—, —CH=N—CH=CH— or —CH=CH—N=CH—; or wherein -a¹=a²-a³=a⁴- is a bivalent radical of formula —CH=CH—CH=CH— or —CH=N—CH=CH—.

Subgroups VIII of the compounds of formula (I) are those compounds of formula (I), or any subgroup of compounds of formula (I) specified herein, such as the subgroups I, II, III, IV, V, VI and VII mentioned above, wherein (a) Q is hydrogen or $C_{1-6}$alkyl optionally substituted with a heterocycle or Q is $C_{1-6}$alkyl substituted with both a radical —OR⁴ and a heterocycle; wherein said heterocycle is selected from the group consisting of oxazolidine, thiazolidine, 1-oxo-thiazolidine, 1,1-dioxothiazolidine, morpholinyl, thiomorpholinyl, 1-oxo-thiomorpholinyl, 1,1-dioxothiomorpholinyl, hexahydrooxazepine, hexahydrothiazepine, 1-oxo-hexahydrothiazepine, 1,1-dioxohexahydrothiazepine; wherein each of said heterocyle may be optionally substituted with one or two substituents selected from the group consisting of $C_{1-6}$alkyl, hydroxy$C_{1-6}$alkyl, hydroxy, carboxyl, $C_{1-6}$alkyloxycarbonyl, aminocarbonyl; or (b) Q is hydrogen or $C_{1-6}$alkyl optionally substituted with a heterocycle or Q is $C_{1-6}$alkyl substituted with both a radical —$OR^4$ and a heterocycle; wherein said heterocycle is selected from the group consisting of oxazolidine, thiazolidine, 1-oxo-thiazolidine, 1,1-dioxothiazolidine, morpholinyl, thiomorpholinyl, 1-oxo-thiomorpholinyl, 1,1-dioxothiomorpholinyl; wherein each of said heterocyle may be optionally substituted with one or two substituents selected from the group consisting of $C_{1-6}$alkyl, hydroxy$C_{1-6}$alkyl, hydroxy; or (c) Q is hydrogen or $C_{1-6}$alkyl optionally substituted with a heterocycle or Q is $C_{1-6}$alkyl substituted with both a radical —$OR^4$ and a heterocycle; wherein said heterocycle is selected from the group consisting of oxazolidine, thiazolidine, morpholinyl, thiomorpholinyl; wherein each of said heterocyle may be optionally substituted with one or two $C_{1-6}$alkyl radicals; or (d) Q is $C_{1-6}$alkyl substituted with morpholinyl or thiomorpholinyl.

Preferably in (a)-(d) in the previous paragraph the heterocycles such as oxazolidine, thiazolidine, 1-oxo-thiazolidine, 1,1-dioxothiazolidine, morpholinyl, thiomorpholinyl, etc., are linked by their nitrogen atom to the $C_{1-6}$alkyl on which they are substituted.

Subgroups IX of the compounds of formula (I) are those compounds of formula (I), or any subgroup of compounds of formula (I) specified herein, such as the subgroups I, II, III, IV, V, VI, VII and VIII mentioned above, wherein one or more of Ar is phenyl or phenyl substituted with 1, 2, 3 substituents or with 1, 2 substituents selected from those mentioned in the definition of the compounds of formula (I) or of any subgroup thereof.

Subgroups X of the compounds of formula (I) are those compounds of formula (I), or any subgroup of compounds of formula (I) specified herein, such as the subgroups I, II, III, IV, V, VI, VII, VIII and IX mentioned above, wherein (a) one or more of Ar is phenyl or phenyl substituted with up to 3 substituents, or with up to 2 substituents, or with one substituent, selected from the group consisting of halo, hydroxy, amino, cyano, $C_{1-6}$alkyl, hydroxy$C_{1-6}$alkyl, polyhalo$C_{1-6}$alkyl, amino$C_{1-6}$alkyl, $C_{1-6}$alkyloxy, aminosulfonyl, aminocarbonyl, hydroxycarbonyl, $C_{1-4}$alkylcarbonyl, mono- or di($C_{1-6}$alkyl)amino and $C_{1-6}$alkoxycarbonyl; or (b) one or more of Ar is phenyl or phenyl substituted with up to 3 substituents, or with up to 2 substituents, or with one substituent, selected from the group consisting of halo, hydroxy, amino, cyano, $C_{1-6}$alkyl, trifluoromethyl, $C_{1-6}$alkyloxy, mono- and di($C_{1-6}$alkyl)amino; or (c) one or more of Ar is phenyl or phenyl substituted with up to 3 substituents, or with up to 2 substituents, or with one substituent, selected from halo, hydroxy, $C_{1-6}$alkyl, hydroxy$C_{1-6}$alkyl, trifluormethyl, and $C_{1-6}$alkyloxy; or (d) one or more of Ar is phenyl or phenyl substituted with up to 3 substituents, or with up to 2 substituents, or with one substituent, selected from the group consisting of halo, hydroxy, $C_{1-6}$alkyl, trifluoromethyl and $C_{1-6}$alkyloxy; or (e) one or more of Ar is phenyl or phenyl substituted with up to 3 substituents, or with up to 2 substituents, or with one substituent, selected from halo, hydroxy, $C_{1-6}$alkyl and $C_{1-6}$alkyloxy; or (f) one or more of Ar is phenyl or phenyl substituted with up to 3 substituents, or with up to 2 substituents, or with one substituent, selected from halo and $C_{1-6}$alkyl.

Certain embodiments of this invention are groups of compounds of formula (I) or subgroups of compounds of formula (I) as specified herein wherein Ar-containing radicals in $R^2$ are as specified in (a)-(f) in the previous paragraph. Certain embodiments of this invention are groups of compounds of formula (I) or subgroups of compounds of formula (I) as specified herein wherein Ar in $R^1$ is as specified in (a)-(f) in the previous paragraph.

The compounds of formula (I) or any of the subgroups thereof can be prepared as in the following reaction scheme.

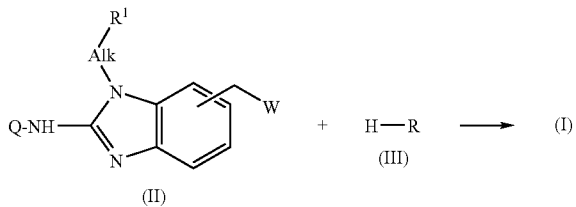

In the above scheme the intermediate H—R (III) is either

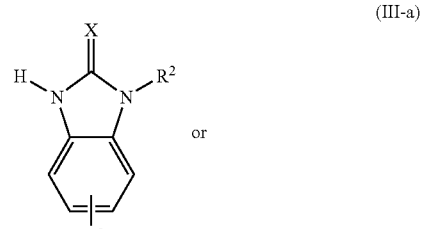

or

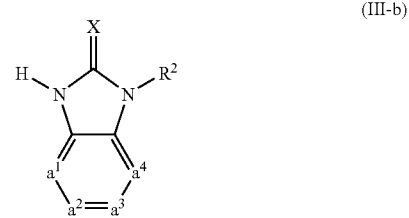

In this scheme Q, Alk, R', $R^2$, $R^3$ have the meanings defined above for the compounds of formula (I) or of any of the subgroups thereof. W is an appropriate leaving group, such as tosylate, mesylate or halo, preferably it is chloro or bromo. In (III-b) the aromatic nitrogen in $a^1=a^2-a^3=a^4$ reacts with the —$CH_2W$ moiety thus forming a pyridinium group. The reaction illustrated in this scheme may be conducted in a suitable solvent in the presence of a base such as an alkali metal carbonate, hydroxide or hydride, e.g. sodium, potassium or cesium carbonate, sodium potassium hydroxide or hydride; or an organic base such as a trialkylamine, e.g. triethylamine. Suitable solvents for this reaction are for example ethers, e.g. THF, dioxane; halogenated hydrocarbons, e.g. dichloromethane, $CHCl_3$; toluene; polar aprotic solvents such as DMF, DMSO, DMA and the like.

Compounds of formula (I) may be converted into each other following art-known functional group transformation reactions, comprising those described hereinafter.

Cyano groups may be reduced to aminomethylene groups, which may be alkylated. Hydroxycarbonyl groups may be esterified to $C_{1-4}$alkyloxycarbonyl groups or vice verse the latter may be hydrolysed to obtain the former.

Some of the functional groups in the intermediates in the above scheme or in the reaction schemes describing the synthesis of the intermediates may be protected. A hydroxyl group may be protected with a benzyl group which is removed afterwards by catalytic hydrogenation.

A number of the intermediates used to prepare the compounds of formula (I) are known compounds or are analogs of known compounds, which can be prepared following modifications of art-known methodologies readily accessible to the skilled person. A number of preparations of intermediates are given hereafter in somewhat more detail.

The intermediates of formula (II) can be prepared from the corresponding hydroxymethylene substituted benzimidazoles of formula (V) by reacting the latter with a suitable leaving group introducing agent such as a halogenating agent, e.g. $SOCl_2$ or $POCl_3$, whereby the hydroxymethylene group is converted to the corresponding halomethylene group. The intermediates (V) can be obtained from the corresponding esters (IV) by a reduction reaction, e.g. with $LiAlH_4$. This reaction sequence is illustrated by the following scheme in which $R^a$ represents a $C_{1-6}$alkyl radical, which preferably is methyl or ethyl.

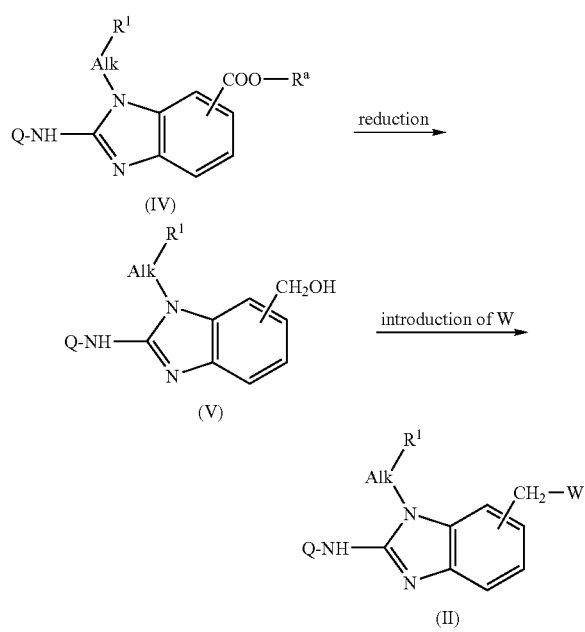

The intermediates (IV) can be obtained as outlined in the following reaction sequence, wherein $R^a$ is as specified above.

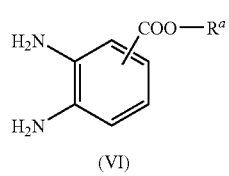

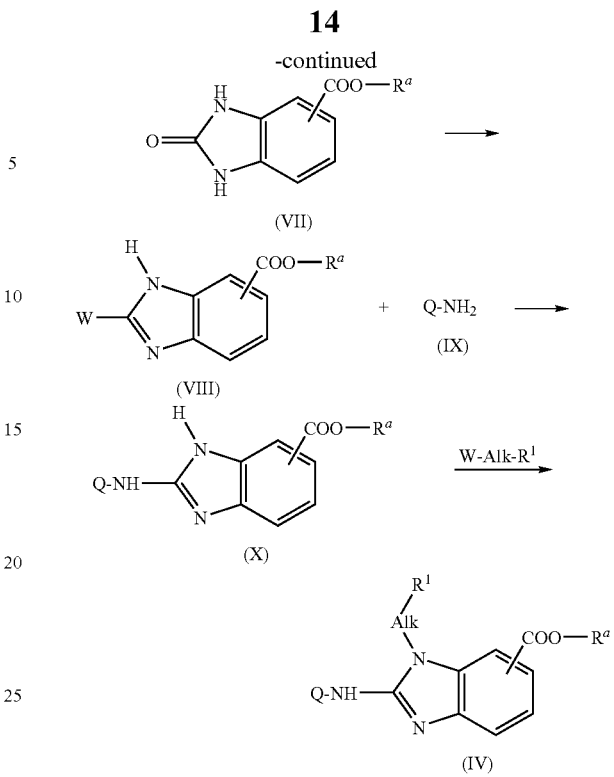

In a first step, a diaminobenzene (VI) is cyclized with urea in a suitable solvent, e.g. xylene, to yield a benzimidazolone (VII). The latter is converted to a benzimidazole derivative (VIII) wherein W is a leaving group as specified above, in particular by reaction of (VII) with a suitable halogenating agent, for example $POCl_3$, and the resulting intermediate (VIII) is reacted with the amine derivative (IX) to obtain intermediate (X). The latter is converted to intermediates (IV) by a N-alkylation reaction.

The intermediates (V) can also be prepared by reacting a diamino benzene of formula

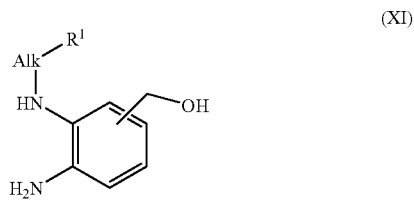

with cyanogen bromide in a suitable solvent such as a alcohol, e.g. methanol or ethanol.

The intermediates (III-a) or (III-b) are either known compounds or can be prepared using the following procedures illustrated herebelow for the preparation of (III-a). The intermediates (III-b) may be prepared in an analogous procedure.

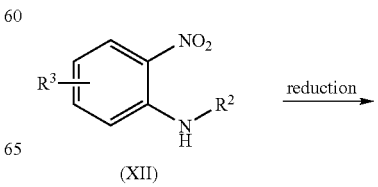

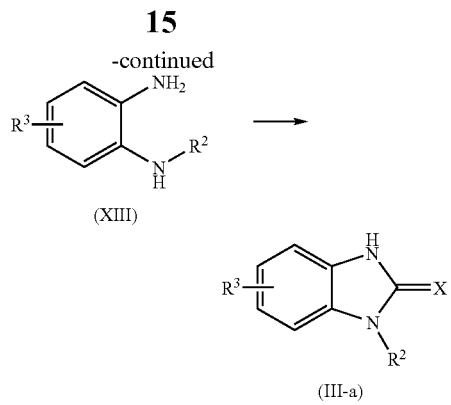

(XIII)

(III-a)

The nitro group in (XII) is reduced using an appropriate reductant, e.g. Raney Ni in the presence of hydrogen, in a suitable solvent such as an alcohol, e.g. methanol or ethanol. The resulting intermediate (XIII) is reacted with a C=X introducing reagent to yield (XIV). C=X introducing reagents that can be used are urea, thiourea or diimidazolyl carbonyl. Suitable solvents for this reaction comprise aromatic hydrocarbons such as benzene, toluene, xylene; ethers such as dioxin or THF.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) as prepared in the hereinabove described processes are generally racemic mixtures of enantiomers which can be separated from one another following art-known resolution procedures. The racemic compounds of formula (I), which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

In a further aspect, the present invention concerns a pharmaceutical composition comprising a therapeutically effective amount of a compound of formula (I) as specified herein, or a compound of any of the subgroups of compounds of formula (I) as specified herein, and a pharmaceutically acceptable carrier. A therapeutically effective amount in this context is an amount sufficient to prophylaxictically act against, to stabilize or to reduce viral infection, and in particular RSV viral infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula (I), as specified herein, or of a compound of any of the subgroups of compounds of formula (I) as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of formula (I) and a pharmaceutically acceptable carrier. Preferably, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula (I) show antiviral properties. Viral infections treatable using the compounds and methods of the present invention include those infections brought on by ortho- and paramyxoviruses and in particular by human and bovine respiratory syncytial virus (RSV). A number of the compounds of this invention moreover are active against mutated strains of RSV. Additionally, many of the compounds of this invention show a favorable pharmacokinetic profile and have attractive properties in terms of bioavailabilty, including an acceptable half-life, AUC and peak values and lacking unfavourable phenomena such as insufficient quick onset and tissue retention.

The in vitro antiviral activity against RSV of the present compounds was tested in a test as described in the experimental part of the description, and may also be demonstrated in a virus yield reduction assay. The in vivo antiviral activity against RSV of the present compounds may be demonstrated in a test model using cotton rats as described in Wyde et al. (Antiviral Research (1998), 38, 31-42).

Due to their antiviral properties, particularly their anti-RSV properties, the compounds of formula (I) or any subgroup thereof, the addition salts and stereochemically isomeric forms, are useful in the treatment of individuals experiencing a viral infection, particularly a RSV infection, and for the prophylaxis of these infections. In general, the compounds of the present invention may be useful in the treatment of warm-blooded animals infected with viruses, in particular the respiratory syncytial virus.

The compounds of the present invention or any subgroup thereof may therefore be used as medicines. Said use as a medicine or method of treatment comprises the systemic administration to viral infected subjects or to subjects susceptible to viral infections of an amount effective to combat the conditions associated with the viral infection, in particular the RSV infection.

The present invention also relates to the use of the present compounds or any subgroup thereof in the manufacture of a medicament for the treatment or the prevention of viral infections, particularly RSV infection. Said treatment or prevention is in patient populations such as warm-blooded animals, particularly humans, more particularly children, still more particularly in children younger than two years of age. Other patient populations for said treatment and prevention are children at a high risk of RSV infection such as children with congenital heart defects, bronchopulmonary dysplasia, premature infants and infants with immune deficiency diseases; furthermore children or adults suffering from chronic long disease, in particular children or adults suffering from asthma, chronic obstructive pulmonary disorder (COPD) or immunodeficiency, the elderly or persons in long term care facilities. Still other patient populations are patients with immunodeficiency or under suppressed immunology. The latter comprise patients undergoing transplantation such as organ transplantation or particularly bone marrow transplantation.

The present invention furthermore relates to a method of treating a warm-blooded animal infected by a virus, or being at risk of infection by a virus, wherein the virus in particular is RSV, said method comprising the administration of an anti-virally effective amount of a compound of formula (I), as specified herein, or of a compound of any of the subgroups of compounds of formula (I), as specified herein. Said warm-blooded animals comprise any of the patient populations mentioned in the previous paragraph.

In general it is contemplated that an antiviral effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

Also, the combination of another antiviral agent and a compound of formula (I) can be used as a medicine. Thus, the present invention also relates to a product containing (a) a compound of formula (I), and (b) another antiviral compound, as a combined preparation for simultaneous, separate or sequential use in antiviral treatment. The different drugs may be combined in a single preparation together with pharmaceutically acceptable carriers. For instance, the compounds of the present invention may be combined with interferon-beta or tumor necrosis factor-alpha in order to treat or prevent RSV infections.

EXAMPLES

The following examples are intended to illustrate the present invention and not to limit it thereto. The terms 'compound a-6', 'compound c-4', etc. used in these examples refers to the same compounds in the tables.

The compounds were identified by LC/MS using the following equipment:

LCT: electrospray ionisation in positive mode, scanning mode from 100 to 900 amu; Xterra MS C18 (Waters, Milford, Mass.) 5 μm, 3.9×150 mm; flow rate 1 ml/min. Two mobile phases (mobile phase A: 85% 6.5 mM ammonium acetate+ 15% acetonitrile; mobile phase B: 20% 6.5 mM ammonium acetate+80% acetonitrile) were employed to run a gradient from 100% A for 3 min to 100% B in 5 min, 100% B for 6 min to 100% A in 3 min, and equilibrate again with 100% A for 3 min.

ZQ: electrospray ionisation in both positive and negative (pulsed) mode scanning from 100 to 1000 amu; Xterra RP C18 (Waters, Milford, Mass.) 5 μm, 3.9×150 mm; flow rate 1 ml/min. Two mobile phases (mobile phase A: 85% 6.5 mM ammonium acetate+15% acetonitrile; mobile phase B: 20% 6.5 mM ammonium acetate+80% acetonitrile) were employed to run a gradient condition from 100% A for 3 min to 100% B in 5 min, 100% B for 6 min to 100% A in 3 min, and equilibrate again with 100% A for 3 min.

Example 1

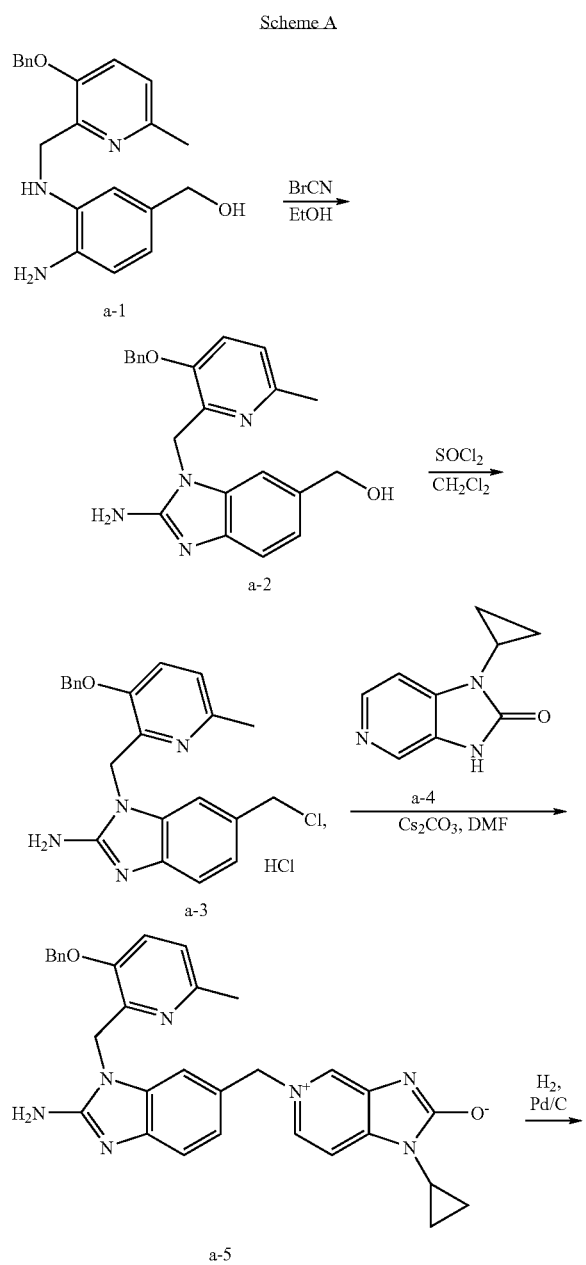

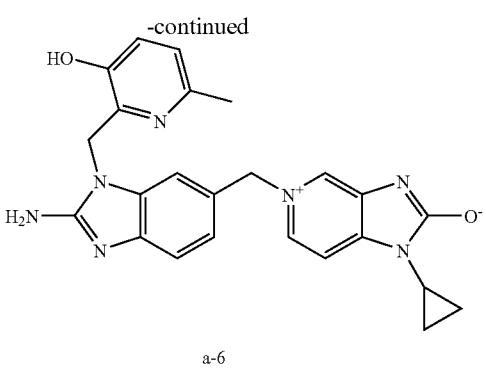

A mixture of a-1 (0.0083 mol) and BrCN (0.0091 mol) in ethanol (50 ml) was stirred and refluxed for 1 hour, then cooled to room temperature and the solvent was evaporated. The residue was taken up in $CH_2Cl_2$. The organic layer was washed with $K_2CO_3$ 10% in water, dried (over $MgSO_4$), filtered and the solvent was evaporated. The residue (3 g) was crystallized from $CH_3CN$. The precipitate was filtered off and dried, yielding 2.2 g of intermediate a-2 (71%).

$SOCl_2$ (0.0042 mol) was added drop wise to a solution of a-3 (0.0021 mol) in $CH_2Cl_2$ (10 ml) at 0° C. The mixture was stirred at room temperature for 2 hours, and then evaporated. The residue was taken up in diethyl ether. The precipitate was filtered, rinsed with diethyl ether and dried, yielding 0.99 g of intermediate a-3 (HCl salt, 100%).

A mixture of a-3 (0.0021 mol), a-4 (0.0031 mol) and $Cs_2CO_3$ (0.0074 mol) in DMF (20 ml) was stirred at 80° C. for 2 hours, and then evaporated. The residue was taken up in $CH_2Cl_2/CH_3OH$. The organic layer was washed with $K_2CO_3$ 10% in water, dried (over $MgSO_4$), filtered and the solvent was evaporated until dryness. The residue (1.7 g) was purified by column chromatography over silica gel (eluent: $CH_2Cl_2/CH_3OH/NH_4OH$ (88/11/1); 15-40 μm). Two fractions were collected and the solvent was evaporated, yielding 0.58 g of intermediate a-5 (51%).

A mixture of a-5 (0.0008 mol) and Pd/C (0.25 g) in $CH_3OH$ (10 ml) was hydrogenated at room temperature for 6 hours, then filtered over celite. Celite was rinsed with $CH_2Cl_2/CH_3OH$. The filtrate was evaporated. The residue (0.4 g) was purified by column chromatography over silica gel (eluent: $CH_2Cl_2/CH_3OH/NH_4OH$ (85/14/1)). The pure fractions were collected and the solvent was evaporated. The residue (0.4 g) was crystallized from 2-propanone. The precipitate was filtered off and dried. Yield: 0.203 g of final compound a-6 (68%, melting point: 228° C.).

Example 2

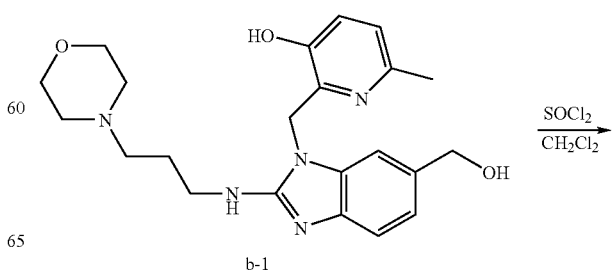

-continued

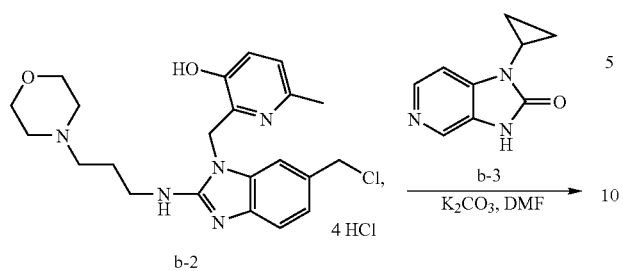

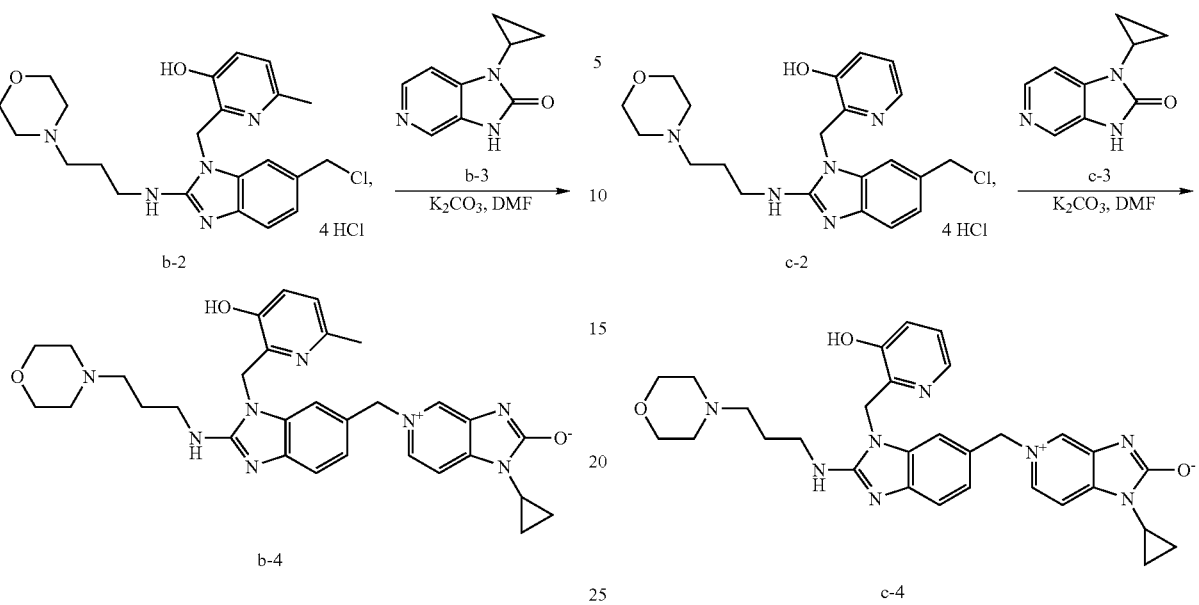

SOCl$_2$ (0.81 ml) was added drop wise to a mixture of b-1 (0.0006 mol) in CH$_2$Cl$_2$ (10 ml) at 5° C. The mixture was stirred at 5° C. for 2 hours, then brought to room temperature and stirred for 12 hours. The solvent was evaporated until dryness, yielding 0.42 g of intermediate b-2 (HCl salt, 100%).

A mixture of b-2 (0.0006 mol), b-3 (0.0009 mol) and K$_2$CO$_3$ (0.0015 mol) in DMF (3 ml) was stirred at 80° C. for 4 hours, and then poured into H$_2$O. The aqueous layer was saturated with K$_2$CO$_3$ powder, and then extracted with ethylacetate/CH$_3$OH. The organic layer was separated, dried (over MgSO$_4$), filtered and the solvent was evaporated. The residue (0.5 g) was purified by column chromatography over silica gel (eluent: CH$_2$Cl$_2$/CH$_3$OH/NH$_4$OH (80/20/0.5); 10 μm). The pure fractions were collected and the solvent was evaporated. The residue (0.5 g) was purified by column chromatography over silica gel (eluent: CH$_2$Cl$_2$/CH$_3$OH/NH$_4$OH (80/20/1.5); 10 μm). The pure fractions were collected and the solvent was evaporated. The residue (0.1 g) was crystallized from CH$_3$CN/CH$_3$OH. The precipitate was filtered off and dried. Yield: 0.06 g of final compound b-4 (17%, melting point: 227° C.).

SOCl$_2$ (0.0018 mol) was added to a mixture of c-1 (0.0003 mol) in CH$_2$Cl$_2$ (20 ml) at 5° C. The mixture was stirred at 5° C. for 2 hours, and then stirred at room temperature for 12 hours. The solvent was evaporated until dryness. The residue was taken up in diisopropylether. The mixture was evaporated, yielding: 0.21 g of intermediate c-2 (HCl salt, 100%).

A mixture of c-2 (0.0006 mol), c-3 (0.0009 mol) and K$_2$CO$_3$ (0.0015 mol) in DMF (3 ml) was stirred at 80° C. for 4 hours, poured into H$_2$O, saturated with K$_2$CO$_3$ powder and extracted with ethylacetate/CH$_3$OH (few). The organic layer was separated, dried (over MgSO$_4$), filtered and the solvent was evaporated. The residue (0.6 g) was purified by column chromatography over silica gel (eluent: CH$_2$Cl$_2$/CH$_3$OH/NH$_4$OH (85/15/1.5); 10 μm). The pure fractions were collected and the solvent was evaporated. Yield: 0.1 g. This fraction was crystallized from CH$_3$CN/CH$_3$OH. The precipitate was filtered off and dried. Yield: 0.045 g of final compound c-4 (13%, melting point: 175° C.).

Example 4

Example 3

Scheme C

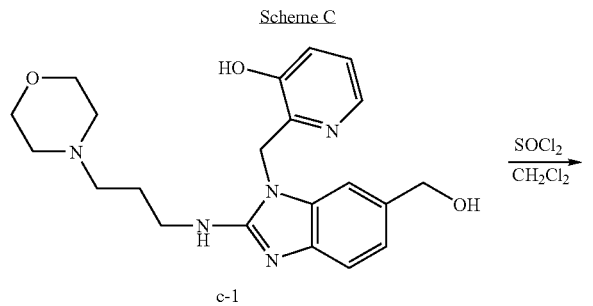

Scheme D

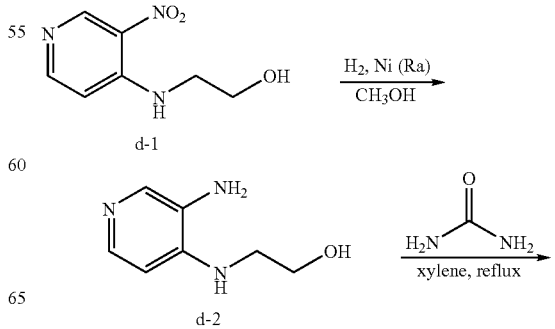

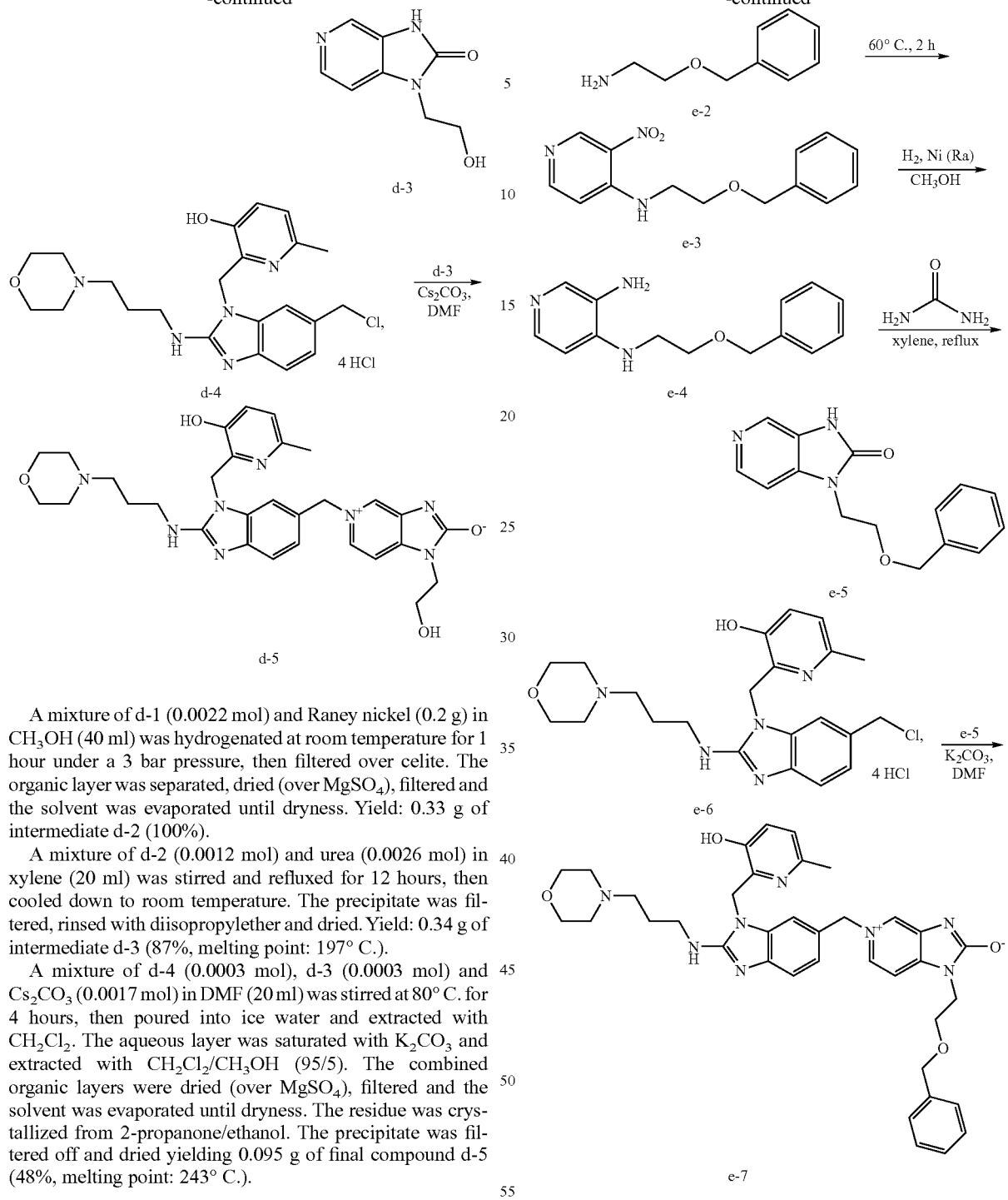

A mixture of d-1 (0.0022 mol) and Raney nickel (0.2 g) in CH$_3$OH (40 ml) was hydrogenated at room temperature for 1 hour under a 3 bar pressure, then filtered over celite. The organic layer was separated, dried (over MgSO$_4$), filtered and the solvent was evaporated until dryness. Yield: 0.33 g of intermediate d-2 (100%).

A mixture of d-2 (0.0012 mol) and urea (0.0026 mol) in xylene (20 ml) was stirred and refluxed for 12 hours, then cooled down to room temperature. The precipitate was filtered, rinsed with diisopropylether and dried. Yield: 0.34 g of intermediate d-3 (87%, melting point: 197° C.).

A mixture of d-4 (0.0003 mol), d-3 (0.0003 mol) and Cs$_2$CO$_3$ (0.0017 mol) in DMF (20 ml) was stirred at 80° C. for 4 hours, then poured into ice water and extracted with CH$_2$Cl$_2$. The aqueous layer was saturated with K$_2$CO$_3$ and extracted with CH$_2$Cl$_2$/CH$_3$OH (95/5). The combined organic layers were dried (over MgSO$_4$), filtered and the solvent was evaporated until dryness. The residue was crystallized from 2-propanone/ethanol. The precipitate was filtered off and dried yielding 0.095 g of final compound d-5 (48%, melting point: 243° C.).

Example 5

Scheme E

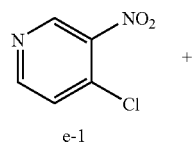

A mixture of e-1 (0.0037 mol) and e-2 (0.0151 mol) was stirred at 60° C. for 2 hours, then purified by column chromatography over silica gel (eluent: CH$_2$Cl$_2$/CH$_3$OH (98/2); 15 μm). The pure fractions were collected and the solvent was evaporated. Yield: 1 g of intermediate e-3 (100%).

A mixture of e-3 (0.0036 mol) and Raney nickel (1 g) in CH$_3$OH (30 ml) was hydrogenated at room temperature for 30 minutes under a 3 bar pressure, then filtered over celite. Celite was rinsed with CH$_3$OH. The filtrate was evaporated. Yield: 0.3 g of intermediate e-4 (34%).

A mixture of e-4 (0.0006 mol) and urea (0.0007 mol) in xylene (10 ml) was stirred and refluxed for 12 hours, then cooled down to room temperature. The precipitate was filtered off and dried. Yield: 0.1 g of intermediate e-5 (62%).

A mixture of e-6 (0.0006 mol), e-5 (0.0006 mol) and K$_2$CO$_3$ (0.003 mol) in DMF (20 ml) was stirred at 80° C. for 4 hours, then poured into ice water, saturated with K$_2$CO$_3$ powder and extracted with CH$_2$Cl$_2$ and CH$_3$OH. The organic layer was separated, dried (over MgSO$_4$), filtered and the solvent was evaporated until dryness. The residue was purified by column chromatography over silica gel (eluent: CH$_2$Cl$_2$/CH$_3$OH/NH$_4$OH (90/10/0.5); 15 µm). The pure fractions were collected and the solvent was evaporated. The residue (0.12 g, 30%) was crystallized from 2-propanone/CH$_3$CN/diisopropylether. The precipitate was filtered off and dried. Yield: 0.03 g of final compound e-7 (13%, melting point: 173° C.).

Example 6

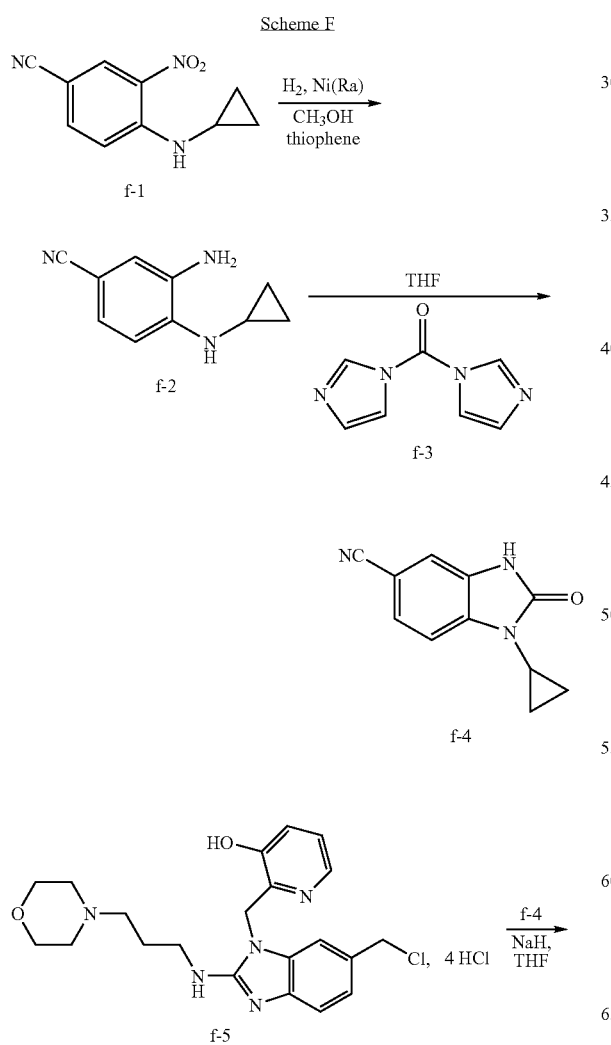

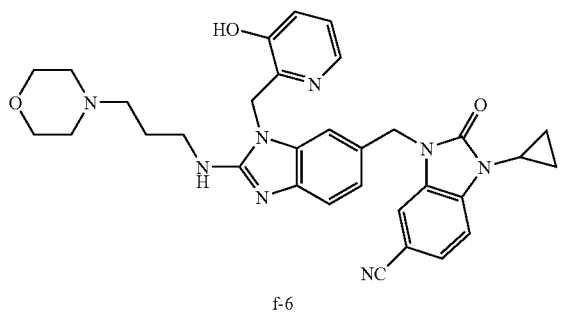

A mixture of f-1 (0.0148 mol), Raney nickel (3 g) and thiophene (0.1 ml) in CH$_3$OH (50 ml) was hydrogenated at room temperature for 1 hour under a 1.5 bar pressure, then filtered over celite. Celite was rinsed with CH$_3$OH. The filtrate was evaporated, yielding 2.8 g of intermediate f-2 (100%).

A mixture of f-2 (0.0132 mol) and f-3 (0.0132 mol) in THF (25 ml) was stirred at room temperature for 2 hours. The solvent was evaporated. The residue was taken up in CH$_2$Cl$_2$ and washed with H$_2$O. The organic layer was dried (over MgSO$_4$), filtered and concentrated. The residue (3.5 g) was purified by column chromatography over silica gel (eluent: CH$_2$Cl$_2$/CH$_3$OH/NH$_4$OH (96/4/0.2); 15-40 µm). The pure fractions were collected and the solvent was evaporated, yielding 1.04 g of intermediate f-4 (39%).

NaH 60% in oil (0.00205 mol) was added drop wise to a solution of f-4 (0.00205 mol) in THF (3 ml) at 0° C. under N$_2$ flow. The reaction was stirred for 30 min at this temperature and f-5 was then added. The reaction was stirred at room temperature under N$_2$ flow for 1.5 hour, and then hydrolyzed very carefully with ice. The solution was saturated with K$_2$CO$_3$ powder and extracted with ethylacetate. The organic layer was dried (over MgSO$_4$), filtered and concentrated. The residue (0.7 g) was purified by column chromatography over silica gel (eluent: CH$_2$Cl$_2$/CH$_3$OH/NH$_4$OH (90/10/0.5)). The pure fractions were collected and the solvent was evaporated. Yield: 0.036 g of final compound f-6 (9%, melting point>250° C.).

Example 7

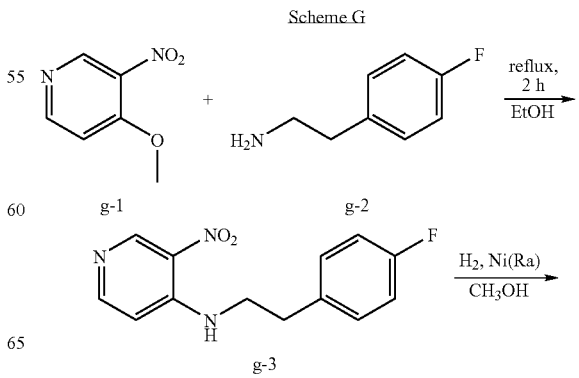

-continued

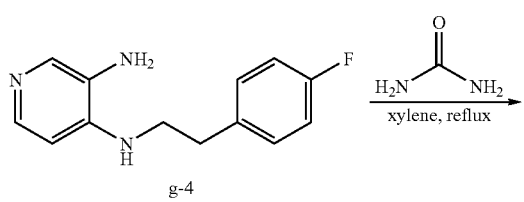

g-4

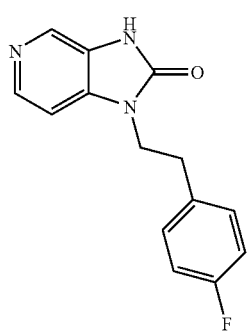

g-5

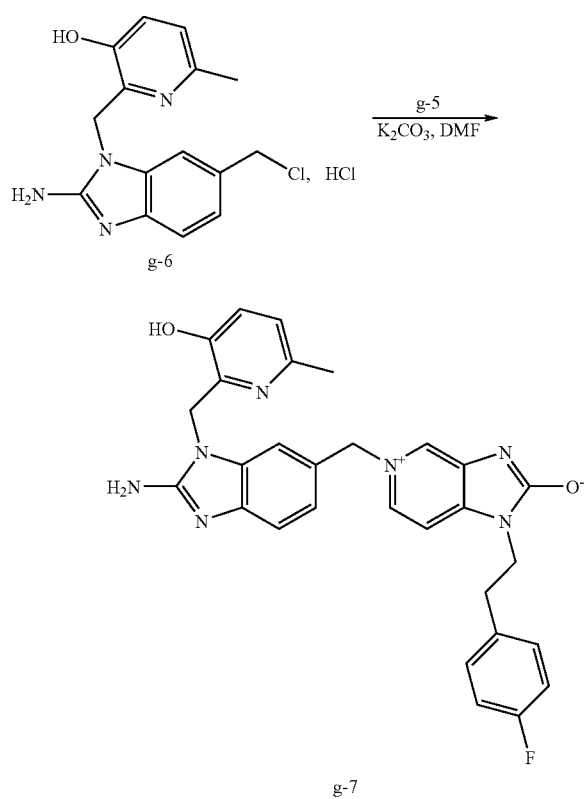

A mixture of g-4 (0.0084 mol) and urea (0.01 mol) in xylene (10 ml) was stirred at 160° C. for 6 hours, then cooled down to room temperature, poured into water and extracted with $CH_2Cl_2$. The organic layer was separated, dried (over $MgSO_4$), filtered and the solvent was evaporated. The residue (1.5 g) was crystallized from $CH_3CN$. The precipitate was filtered off and dried, yielding 0.67 g of intermediate g-5 (31%, melting point: 169° C.).

A mixture of g-6 (0.0011 mol), g-5 (0.0011 mol) and $K_2CO_3$ (0.0046 mol) in DMF (5 ml) was stirred at 80° C. for 2 hours, poured into water (the minimum). $CH_2Cl_2$ was added. The organic layer was separated, dried (over $MgSO_4$), filtered and the solvent was evaporated. The residue (0.4 g) was purified by column chromatography over silica gel (eluent: $CH_2Cl_2/CH_3OH/NH_4OH$ 90/10/1; 5 μm). The pure fractions were collected and the solvent was evaporated. The residue (0.13 g) was crystallized from 2-propanone. The precipitate was filtered off and dried, yielding 0.062 g of final compound g-7 (21%, melting point: 245° C.).

Example 8

Scheme H

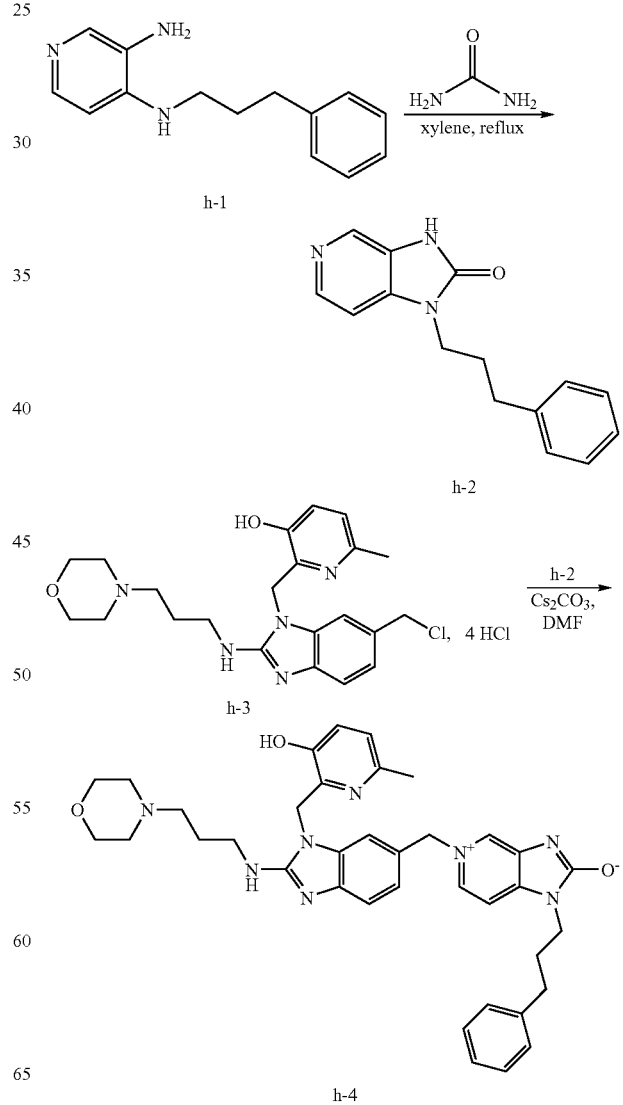

A mixture of g-1 (0.0078 mol) and g-2 (0.0094 mol) in ethanol (10 ml) was stirred and refluxed for 24 hours, then cooled down to 0° C. The precipitate was filtered off, washed with ethanol and dried, yielding 1.8 g of intermediate g-3 (88%, melting point: 154° C.).

A mixture of g-3 (0.068 mol) and Raney nickel (1.8 g) in methanol (50 ml) was hydrogenated for 1 hour under a 3 bar pressure, then filtered over a pad of celite. The filtrate was concentrated under reduced pressure, yielding 1.8 g of intermediate g-4 (100%).

A mixture of h-1 (0.0078 mol) and urea (0.0094 mol) in xylene (10 ml) was stirred at 160° C. for 6 hours, then cooled down to room temperature, poured into water and extracted with $CH_2Cl_2$. The organic layer was separated, dried (over $MgSO_4$), filtered and the solvent was evaporated. The residue (3.5 g) was crystallized from $CH_3CN$. The precipitate was filtered off and dried. The mother layer was purified by column chromatography over silica gel (eluent: $CH_2Cl_2$/$CH_3OH$/$NH_4OH$ 95/5/0.5). The pure fractions were collected and the solvent was evaporated, yielding 0.75 g of intermediate h-2 (38%).

A mixture of h-3 (0.0003 mol), h-2 (0.0005 mol) and $Cs_2CO_3$ (0.0017 mol) in DMF (3 ml) was stirred at 80° C. for 2 hours, and then concentrated under reduced pressure. The residue was taken up in ethylacetate/$CH_3OH$. The organic layer was washed with saturated $K_2CO_3$ solution in water (10 ml), dried (over $MgSO_4$), filtered and the solvent was evaporated. The residue (0.25 g) was purified by column chromatography over silica gel (eluent: $CH_2Cl_2$/$CH_3OH$/$NH_4OH$ 88/12/1.2; 5 μm). The pure fractions were collected and the solvent was evaporated, yielding 0.028 g of final compound h-4 (12%, melting point: 187° C.).

Example 9

A mixture of i-1 (0.0003 mol), i-2 (0.0004 mol) and $Cs_2CO_3$ (0.0017 mol) in DMF (3 ml) was stirred at 80° C. for 2 hours, then concentrated under reduced pressure. The residue was taken up in ethylacetate/$CH_3OH$. The organic layer was washed with saturated $K_2CO_3$ solution in water, dried (over $MgSO_4$), filtered and the solvent was evaporated. The residue (0.4 g) was purified by column chromatography over silica gel (eluent: $CH_2Cl_2$/$CH_3OH$/$NH_4OH$ 87/17/1.7; 5 μm). The pure fractions were collected and the solvent was evaporated. The residue (0.083 g) was dissolved in HCl/2-propanol and converted into the hydrochloric acid salt. The precipitate was filtered off and dried, yielding 0.065 g of final compound I-3 (HCl salt, 22%, melting point: 180° C.).

Example 10

Scheme J

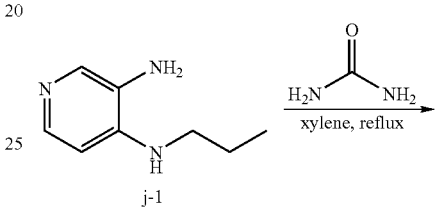

j-1

Scheme I

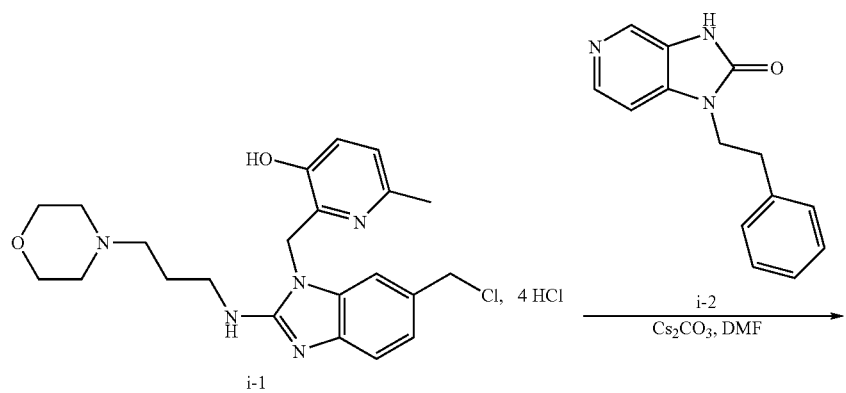

i-1

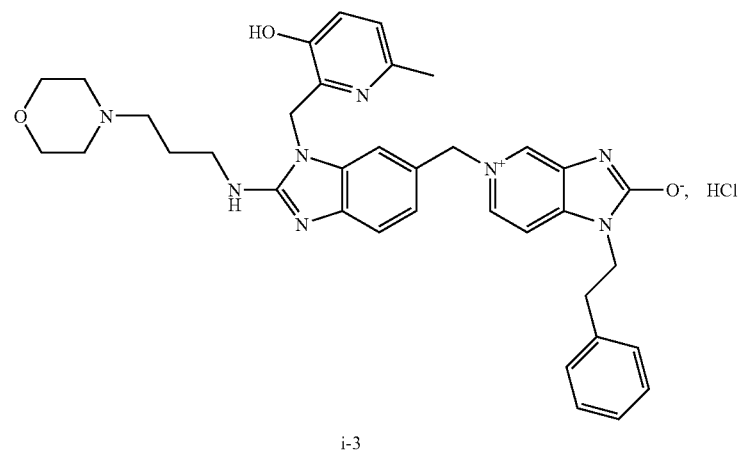

i-3

-continued

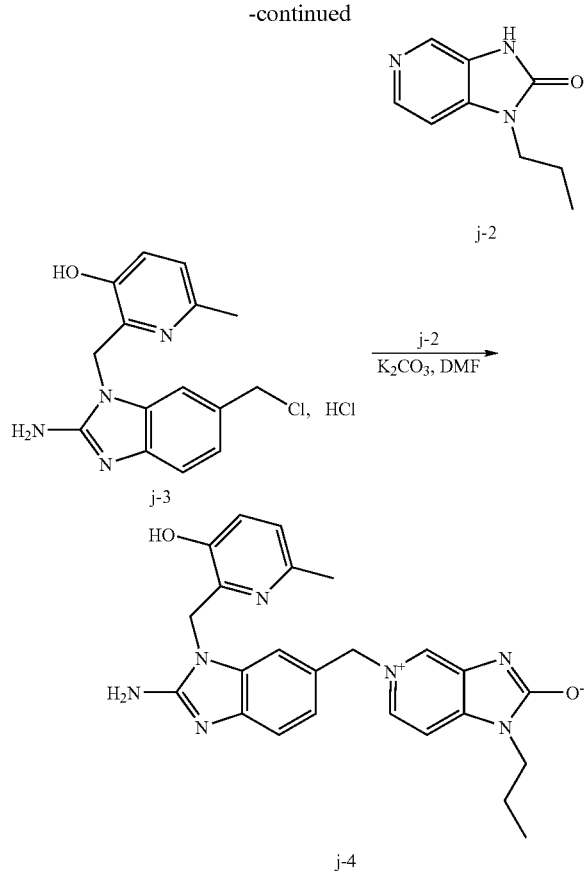

A mixture of j-1 (0.0086 mol) and urea (0.0103 mol) in xylene (10 ml) was stirred at 160° C. for 5 hours, then cooled down to room temperature, poured into water and extracted with CH$_2$Cl$_2$. The organic layer was separated, dried (over MgSO$_4$), filtered and the solvent was evaporated. The residue (2 g) was crystallized from CH$_3$CN (the minimum). The precipitate was filtered off and dried. The residue (0.4 g) was purified by column chromatography over silica gel (eluent: CH$_2$Cl$_2$/CH$_3$OH/NH$_4$OH 90/10/0.5). The pure fractions were collected and the solvent was evaporated, yielding 0.5 g of intermediate j-2 (59%, melting point: 134° C.).

K$_2$CO$_3$ (0.0047 mol) was added to a mixture of j-3 (0.0011 mol) and j-2 (0.0014 mol) in DMF (5 ml). The mixture was stirred at 80° C. for 2 hours, and then concentrated under reduced pressure. The residue was taken up in CH$_2$Cl$_2$/CH$_3$OH. The organic layer was washed with saturated K$_2$CO$_3$ solution in water, dried (over MgSO$_4$), filtered and the solvent was evaporated. The residue (0.7 g) was purified by column chromatography over silica gel (eluent: CH$_2$Cl$_2$/CH$_3$OH/NH$_4$OH 90/10/1; 5 μm). The pure fractions were collected and the solvent was evaporated. The residue (0.2 g) was crystallized from 2-propanone. The precipitate was filtered off and dried, yielding: 0.136 g of final compound j-4 (38%, melting point: 250° C.).

Example 11

Scheme K

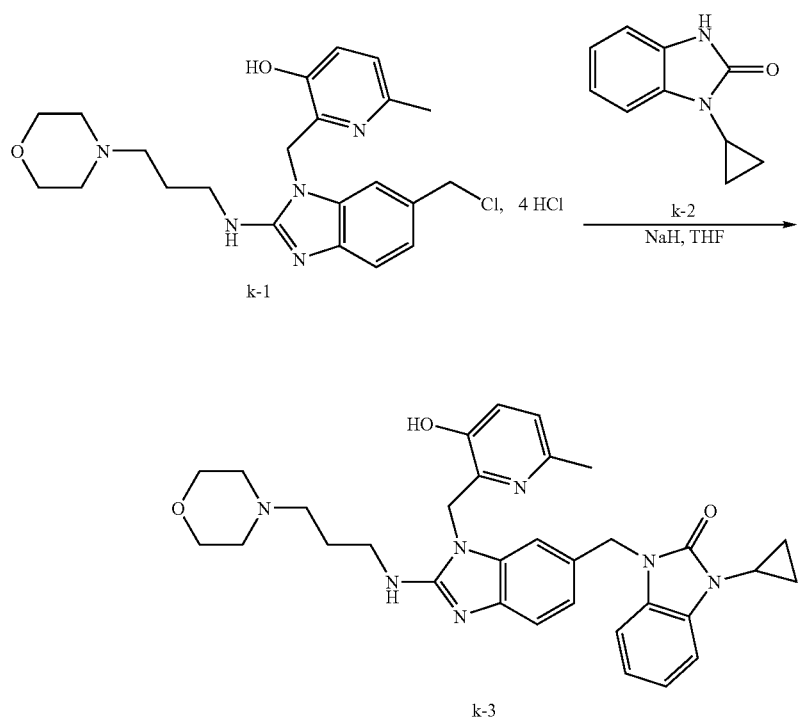

NaH (0.0011 mol) was added at 0° C. to a solution of k-2 (0.0011 mol) in THF (5 ml) under N₂ flow. The mixture was stirred at 5° C. for 30 minutes. k-1 (0.0003 mol) was added. The mixture was stirred at room temperature for 1.5 hours under N₂ flow. The mixture was poured slowly into ice, saturated with K₂CO₃ and extracted with ethylacetate. The organic layer was separated, dried (over MgSO₄), filtered and the solvent was evaporated. The residue (0.3 g) was purified by column chromatography over silica gel (eluent: CH₂Cl₂/CH₃OH/NH₄OH 97/3/0.3 to 86/14/1.4; 5 μm). The pure fractions were collected and the solvent was evaporated, yielding 0.019 g. The residue was crystallized from 2-propanone/diisopropylether. The precipitate was filtered off and dried, yielding 0.017 g of final compound k-3 (8%, melting point: 120° C.).

Example 12

Scheme L

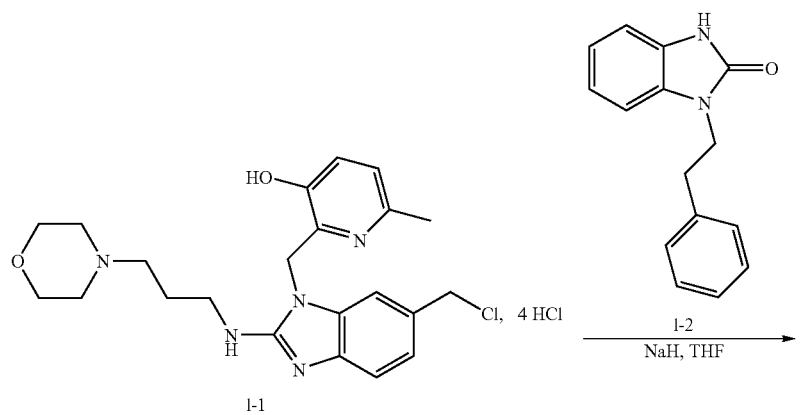

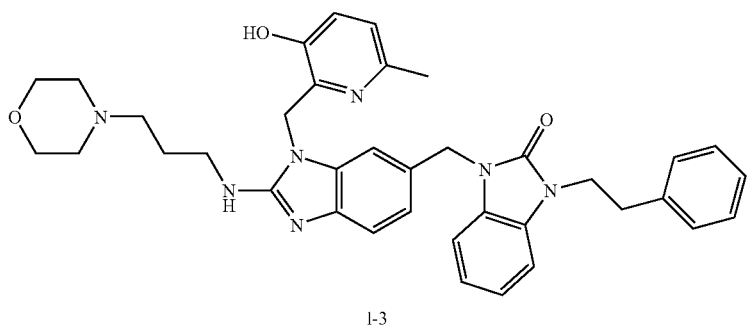

NaH (0.0018 mol) was added at 0° C. to a solution of l-2 (0.0018 mol) in THF (10 ml) under N₂ flow. The mixture was stirred at 5° C. for 30 minutes. l-1 (0.0006 mol) was added. The mixture was stirred at room temperature for 1.5 hours under N₂ flow, poured slowly into ice, saturated with K₂CO₃ and extracted with ethylacetate. The organic layer was separated, dried (over MgSO₄), filtered and the solvent was evaporated. The residue (0.67 g) was purified by column chromatography over silica gel (eluent: CH₂Cl₂/CH₃OH/NH₄OH 96/4/0.3 to 87/13/1.3; 5 μm). The pure fractions were collected and the solvent was evaporated. The residue was crystallized from 2-propanone/diisopropylether. The precipitate was filtered off and dried, yielding 0.036 g of final compound I-3 (10%, melting point: 198° C.).

Following the same procedures there was prepared compound I-4, listed in the table hereafter.

Example 13

Scheme M

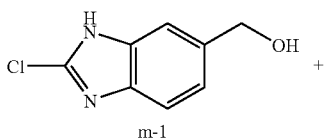

m-1

-continued

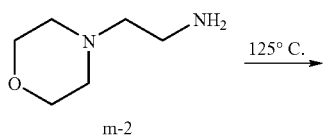

m-2

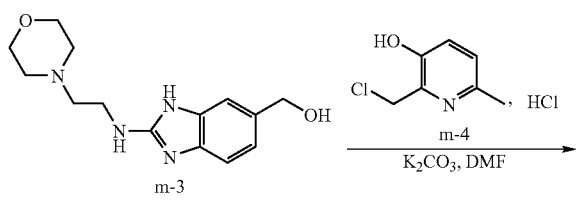

m-3

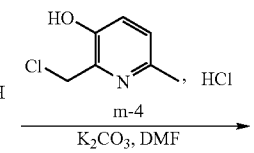

m-4

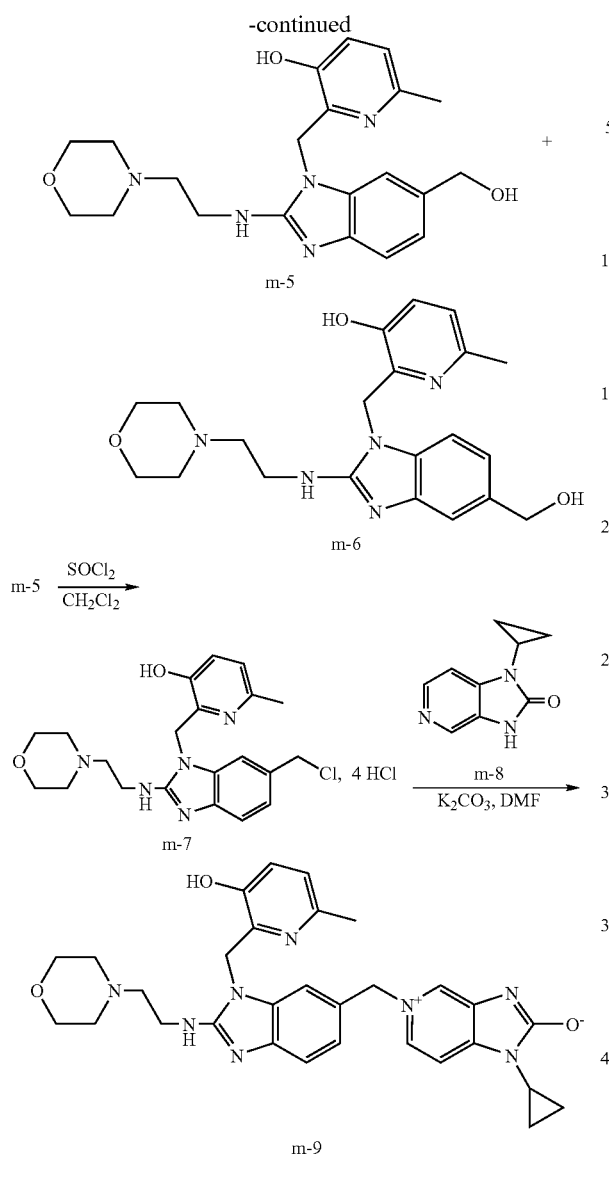

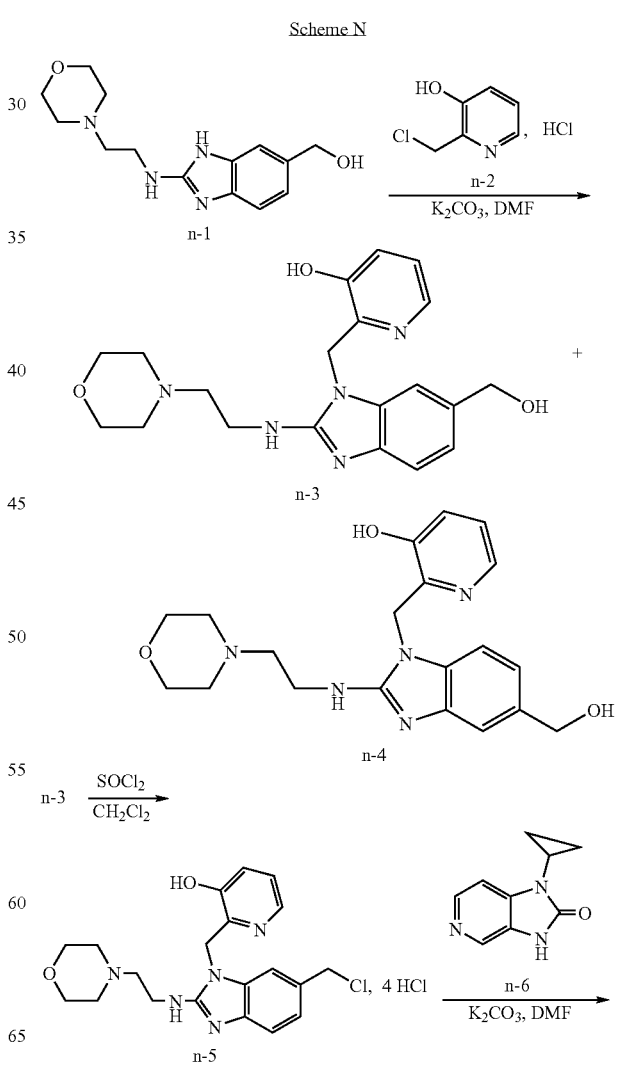

melting point: 190° C.). F2 was crystallized from 2-propanone/CH₃OH. The precipitate was filtered off and dried, yielding: 1.2 g of intermediate m-6 (31%, melting point: 230° C.).

SOCl₂ (0.0019 mol) was added drop wise at 5° C. to a solution of m-5 (0.0003 mol) in CH₂Cl₂ (20 ml). The mixture was stirred at 5° C. for 2 hours, at room temperature for 12 hours and then concentrated under reduced pressure, yielding intermediate m-7 (100%).

A mixture of m-7 (0.0003 mol), m-8 (0.0005 mol) and K₂CO₃ (0.0011 mol) in DMF (20 ml) was stirred at 80° C. for 4 hours and then poured into ice. The solution was saturated with K₂CO₃ and extracted with CH₂Cl₂/CH₃OH. The organic layer was separated, dried (over MgSO₄), filtered and the solvent was evaporated. The residue (0.35 g) was purified by column chromatography over silica gel (eluent: CH₂Cl₂/CH₃OH/NH₄OH 92/8/0.8 to 80/20/2; 5 μm). The pure fractions were collected and the solvent was evaporated. The residue (0.115 g) was crystallized from CH₃OH/diisopropylether. The precipitate was filtered off and dried, yielding 0.089 g of final compound m-9 (43%, melting point: 204° C.).

Example 14

A mixture of m-1 (0.0273 mol) and m-2 (0.1095 mol) was stirred at 125° C. for 5 hours and then poured into a 10% solution of K₂CO₃. The solution was saturated with K₂CO₃ (powder) and extracted with CH₂Cl₂/CH₃OH. The organic layer was separated, dried (over MgSO₄), filtered and the solvent was evaporated. The residue (16 g) was purified by column chromatography over silica gel (eluent: CH₂Cl₂/CH₃OH/NH₄OH 88/12/0.5; 20-45 μm). The pure fractions were collected and the solvent was evaporated, yielding 5.4 g of intermediate m-3 (71%, melting point: 173° C.).

A mixture of m-3 (0.0098 mol), m-4 (0.0117 mol) and K₂CO₃ (0.03 mol) in DMF (30 ml) was stirred at room temperature for 12 h, at 60° C. for 3 hours and then poured into ice water. The solution was saturated with K₂CO₃ and extracted with CH₂Cl₂/CH₃OH. The organic layer was separated, dried (over MgSO₄) and the solvent was evaporated. The residue (5.2 g) was purified by column chromatography over silica gel (eluent: CH₂Cl₂/CH₃OH/NH₄OH 85/14/1; 15-40 μm). Two fractions were collected and the solvent was evaporated, yielding 1.36 g of F1 (35%) and 1.51 g of F2 (39%). F1 was crystallized from 2-propanone. The precipitate was filtered off and dried, yielding: 1.2 g of intermediate m-5 (31%,

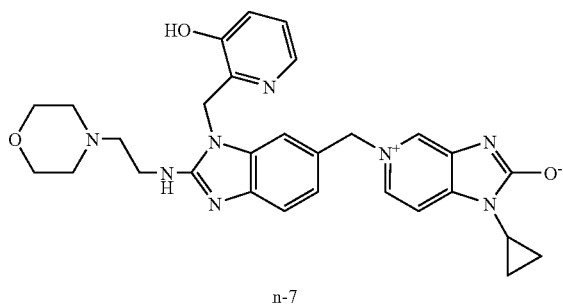

n-7

A mixture of n-1 (0.0098 mol), n-2 (0.0117 mol) and K$_2$CO$_3$ (0.03 mol) in DMF (30 ml) was stirred at room temperature for 12 hours, at 60° C. for 3 hours and then poured into ice. K$_2$CO$_3$ was added and the solution was extracted with CH$_2$Cl$_2$/CH$_3$OH.

The organic layer was separated, dried (over MgSO$_4$), filtered and the solvent was evaporated. The residue (5 g) was purified by column chromatography over silica gel (eluent: CH$_2$Cl$_2$/CH$_3$OH/NH$_4$OH 88/12/1; 15-40 µm). Two fractions were collected and the solvent was evaporated, yielding 1 g of intermediate n-3 (27%, melting point 227° C.) and 1.1 g of intermediate n-4 (29%, melting point 195° C.).

SOCl$_2$ (0.0022 mol) was added drop wise at 5° C. to a solution of n-3 (0.0004 mol) in CH$_2$Cl$_2$ (10 ml). The mixture was stirred at 5° C. for 1 hour, at room temperature for 12 hours and concentrated under reduced pressure. The residue was taken up in diisopropylether. The precipitate was filtered off and dried, yielding 0.215 g of intermediate n-5 (88%).

A mixture of n-5 (0.0003 mol), n-6 (0.0005 mol) and K$_2$CO$_3$ (0.0011 mol) in DMF (7 ml) was stirred at 80° C. for 5 hours, then poured into water. The aqueous layer was saturated with K$_2$CO$_3$ (powder). The organic layer was separated, dried (over MgSO$_4$), filtered and the solvent was evaporated. The residue (0.4 g) was purified by column chromatography over silica gel (eluent: CH$_2$Cl$_2$/CH$_3$OH/NH$_4$OH 93/7/0.7 to 80/20/2; 5 µm). The pure fractions were collected and the solvent was evaporated. The residue was crystallized from CH$_3$OH/diisopropylether. The precipitate was filtered off and dried, yielding 0.016 g of final compound n-7 (8%, melting point 184° C.).

Example 15

Scheme O

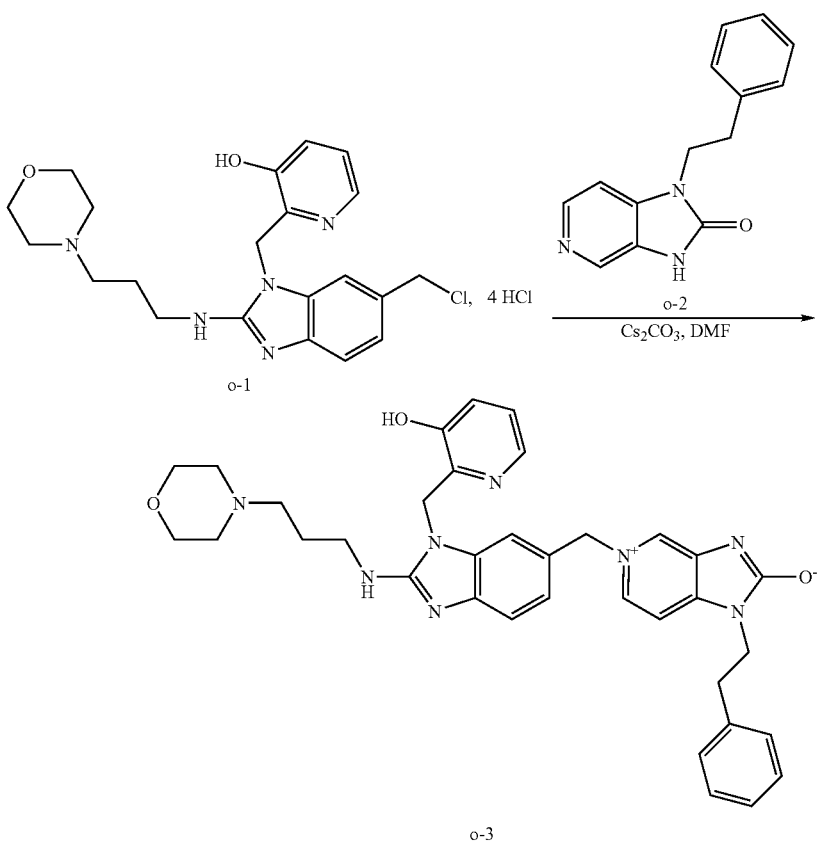

A mixture of o-1 (0.0005 mol), o-2 (0.0005 mol) and Cs$_2$CO$_3$ (0.0026 mol) in DMF (5 ml) was stirred at 80° C. for 2 hours and then concentrated under reduced pressure. The residue was taken up in ethylacetate and CH$_3$OH. The organic layer was washed with a saturated solution of K$_2$CO$_3$, dried (over MgSO$_4$), filtered and the solvent was evaporated. The residue (0.5 g) was purified by column chromatography over silica gel (eluent: CH$_2$Cl$_2$/CH$_3$OH/NH$_4$OH 88/12/1.2; 5 µm). The pure fractions were collected and the solvent was evaporated. The residue 0.054 g) was dissolved in isopropanol and converted into the hydrochloric acid salt. The precipitate was filtered off and dried, yielding: 0.03 g of final compound o-3 (16%, melting point: 170° C.).

Example 16

Scheme P

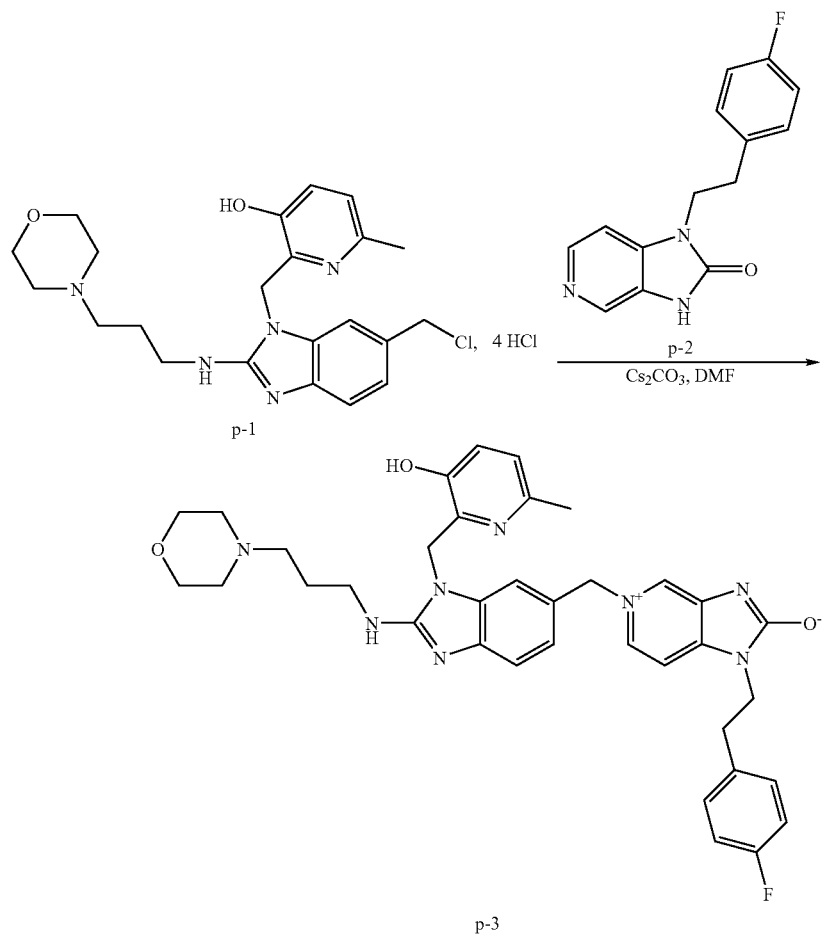

A mixture of p-1 (0.0005 mol), p-2 (0.0007 mol) and Cs$_2$CO$_3$ (0.0026 mol) in DMF (5 ml) was stirred at 80° C. for 2 hours, and then poured into water. CH$_2$Cl$_2$ was added. The organic layer was separated, dried (over MgSO$_4$), filtered and the solvent was evaporated. The residue (0.5 g) was purified by column chromatography over silica gel (eluent: CH$_2$Cl$_2$/ CH$_3$OH/NH$_4$OH 90/10/1; 5 μm). The pure fractions were collected and the solvent was evaporated. The residue (0.15 g) was crystallized from 2-propanone/CH$_3$OH/diethyl ether. The precipitate was filtered off and dried, yielding 0.084 g of final compound p-3 (45%, melting point 230° C.).

Example 17

Scheme Q

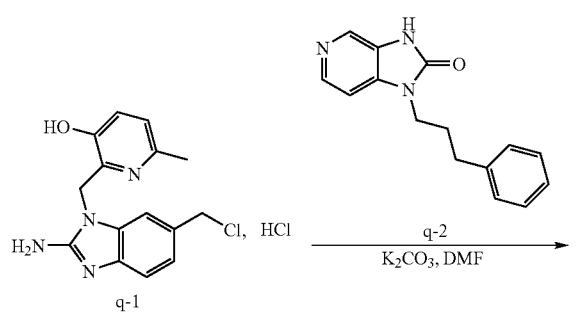

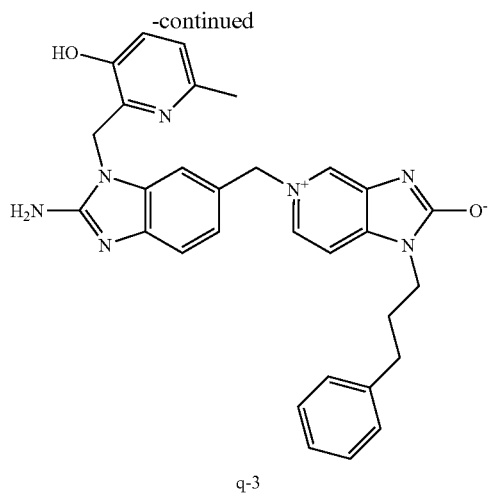

K$_2$CO$_3$ (0.0047 mol) was added to a mixture of q-1 (0.0011 mol) and q-2 (0.0014 mol) in DMF (5 ml). The mixture was stirred at 80° C. for 2 hours, and then concentrated under reduced pressure. The residue was taken up in CH$_2$Cl$_2$/ CH$_3$OH. The organic layer was washed with a saturated solution of K$_2$CO$_3$, dried (over MgSO$_4$), filtered and the solvent was evaporated. The residue (1 g) was purified by column chromatography over silica gel (eluent: CH$_2$Cl$_2$/CH$_3$OH/ NH$_4$OH 90/10/1; 15-40 µm). The pure fractions were collected and the solvent was evaporated. The residue (0.275 g) was crystallized from 2-propanone. The precipitate was filtered off and dried, yielding 0.158 g of final compound q-3 (45%, melting point: 238° C.).

Example 18

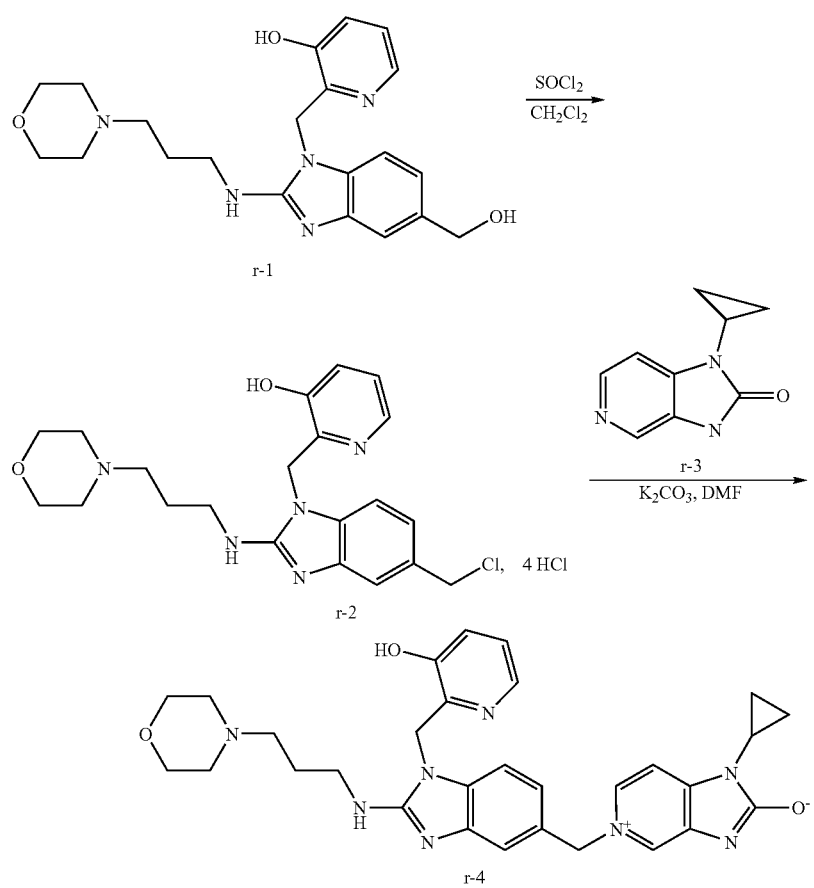

SOCl$_2$ (0.003 mol) was added at 5° C. to a solution of r-2 (0.0006 mol) in CH$_2$Cl$_2$ (25 ml). The mixture was stirred at 5° C. for 2 hours, at room temperature for 12 hours and then concentrated under reduced pressure, yielding intermediate r-2 (100%).

A mixture of r-2 (0.0006 mol), r-3 (0.0009 mol) and K$_2$CO$_3$ (0.0018 mol) in DMF (30 ml) was stirred at 80° C. for 5 hours, poured into ice water, saturated with K$_2$CO$_3$ and extracted with CH$_2$Cl$_2$/CH$_3$OH. The organic layer was separated, dried (over MgSO$_4$), filtered and the solvent was evaporated. The residue (0.5 g) was purified by column chromatography over silica gel (eluent: CH$_2$Cl$_2$/CH$_3$OH/NH$_4$OH 85/15/1.5 to 80/20/2; 10 µm). The pure fractions were collected and the solvent was evaporated. The residue (0.12 g, 35%) was crystallized from 2-propanone/CH$_3$OH. The precipitate was filtered off and dried, yielding 0.08 g of final compound r-4 (23%, melting point 201° C.).

Example 19

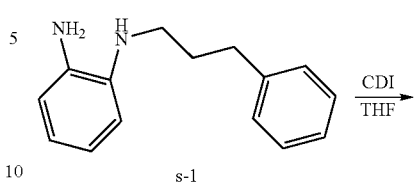

-continued

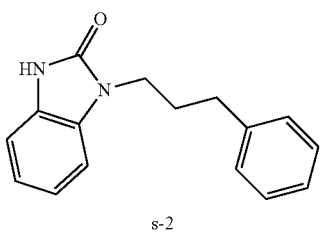

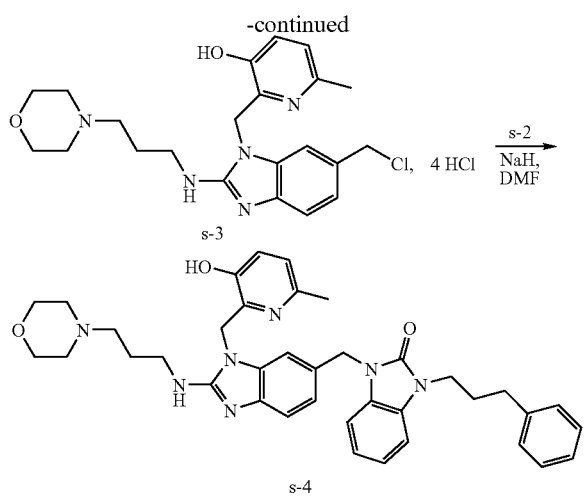

CDI (0.04 mol) was added at room temperature to a solution of s-1 (0.04 mol) in THF (100 ml). The mixture was stirred at room temperature for 3 hours, and then concentrated under reduced pressure. The residue was taken up in $CH_2Cl_2$/$H_2O$. The mixture was extracted with $CH_2Cl_2$. The organic layer was separated, dried (over $MgSO_4$), filtered and the solvent was evaporated. $CH_3CN$ was added. The precipitate was filtered off and dried, yielding 4.6 g of intermediate s-2 (46%).

NaH (0.0024 mol) was added at 5° C. to a solution of s-2 (0.0024 mol) in THF (15 ml) under $N_2$ flow. The mixture was stirred at 5° C. for 30 minutes. s-3 (0.0008 mol) was added. The mixture was stirred at room temperature for 1 hour and 30 minutes under $N_2$ flow, poured into ice slowly. The solution was saturated with $K_2CO_3$ and extracted with ethylacetate. The organic layer was separated, dried (over $MgSO_4$), filtered and the solvent was evaporated. The residue (0.91 g) was purified by column chromatography over silica gel (eluent: $CH_2Cl_2$/$CH_3OH$/$NH_4OH$ 98/2/0.2 to 91/9/0.9; 5 μm). The pure fractions were collected and the solvent was evaporated. The residue 0.057 g) was crystallized from 2-propanone. The precipitate was filtered off and dried, yielding 0.05 g of final compound s-4 (10%, melting point 196° C.).

The following tables list compounds that were prepared according to any one of the above examples.

TABLE 1

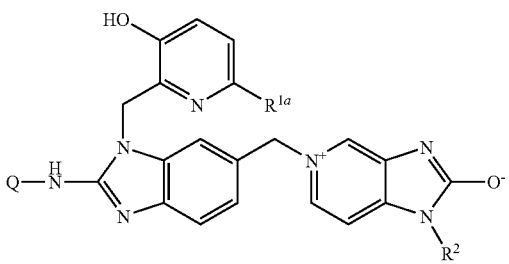

| Comp. Nr. | Q | $R^{1a}$ | $R^2$ | $pEC_{50}$ | MP (° C.) | LC/MS ($MH^+$) |
|---|---|---|---|---|---|---|
| a-6 | H---- | ```CH_3 | ⟩ (cyclopropyl) | 6.95 | 228 | 442 |
| c-4 | morpholine-propyl- | ```H | ⟩ (cyclopropyl) | 5.4 | 175 | 555 |
| b-4 | morpholine-propyl- | ```CH_3 | ⟩ (cyclopropyl) | 7.1 | 227 | 569 |
| d-5 | morpholine-propyl- | ```CH_3 | -CH_2CH_2OH | 6.65 | 243 | 573 |

TABLE 1-continued
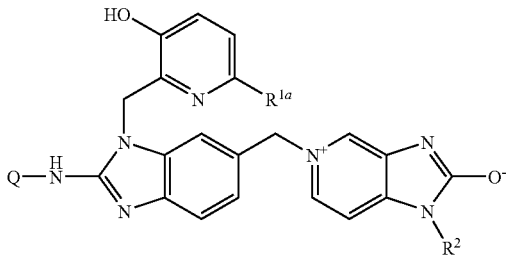
| Comp. Nr. | Q | $R^{1a}$ | $R^2$ | $pEC_{50}$ | MP (° C.) | LC/MS (MH$^+$) |
|---|---|---|---|---|---|---|
| e-7 | 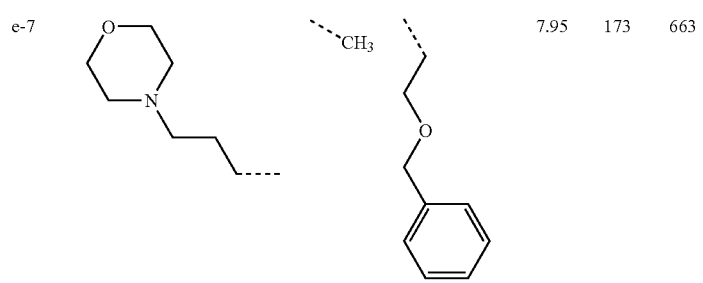 | CH$_3$ | | 7.95 | 173 | 663 |
| m-9 | 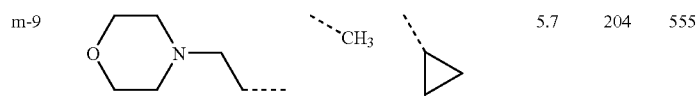 | CH$_3$ | | 5.7 | 204 | 555 |
| n-7 | 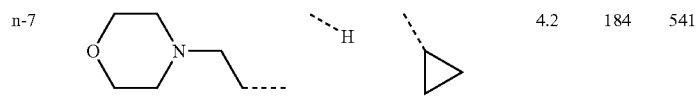 | H | | 4.2 | 184 | 541 |
| i-3 | 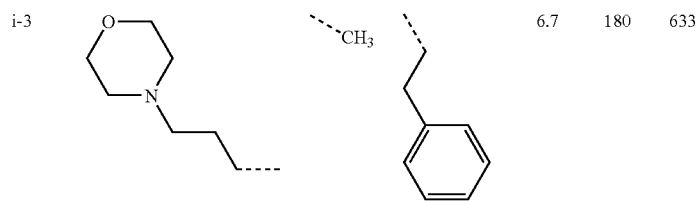 | CH$_3$ | | 6.7 | 180 | 633 |
| h-4 | 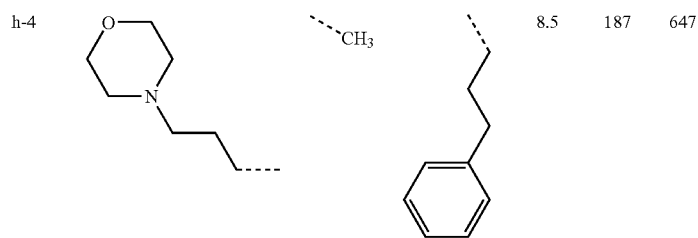 | CH$_3$ | | 8.5 | 187 | 647 |

TABLE 1-continued

| Comp. Nr. | Q | R^1a | R^2 | pEC$_{50}$ | MP (° C.) | LC/MS (MH$^+$) |
|---|---|---|---|---|---|---|
| o-3 | morpholine-propyl | H | phenethyl | 6.25 | 170 | 619 |
| p-3 | morpholine-propyl | CH$_3$ | 4-fluorophenethyl | 7.2 | 230 | 651 |
| g-7 | H | CH$_3$ | 4-fluorophenethyl | 7.85 | 245 | 524 |
| q-3 | H | CH$_3$ | phenylpropyl | 8.15 | 238 | 520 |
| j-4 | H | CH$_3$ | propyl | 7.6 | 250 | 444 |

The dotted line in the above tables represents the bond by which the radical is linked to the rest of the molecule.

TABLE 2

| Comp. Nr. | Q | pEC$_{50}$ | MP (° C.) | LC/MS (MH$^+$) |
|---|---|---|---|---|
| r-4 | (structure) | 4.8 | 201 | 569 |

TABLE 3

(structure)

| Comp. Nr. | R$^{1a}$ | R$^2$ | R$^3$ | pEC$_{50}$ | MP (° C.) | LC/MS (MH$^+$) |
|---|---|---|---|---|---|---|
| k-3 | CH$_3$ | cyclopropyl | H | 8.05 | 120 | 568 |
| l-3 | CH$_3$ | phenethyl | H | 7.35 | 198 | 632 |
| l-4 | CH$_3$ | phenethyl | H | 8 | 196 | 646 |
| f-6 | H | cyclopropyl | CN | 6.85 | >250 | 579 |

The dotted line in the above tables represents the bond by which the radical is linked to the rest of the molecule.

Example 20

In Vitro Screening for Activity Against Respiratory Syncytial Virus

The percent protection against cytopathology caused by viruses (antiviral activity or EC$_{50}$) achieved by tested compounds and their cytotoxicity (CC$_{50}$) are both calculated from dose-response curves. The selectivity of the antiviral effect is represented by the selectivity index (SI), calculated by dividing the CC$_{50}$ (cytotoxic dose for 50% of the cells) by the EC$_{50}$ (antiviral activity for 50% of the cells).

Automated tetrazolium-based colorimetric assays were used for the determination of EC$_{50}$ and CC$_{50}$ of test compounds. Flat-bottom, 96-well plastic microtiter trays were filled with 180 µl of Eagle's Basal Medium, supplemented with 5% foetal calf serum, (FCS), and 20 mM Hepes buffer. Subsequently, stock solutions (7.8× final test concentration) of compounds were added in 45 µL volumes to a series of triplicate wells to allow simultaneous evaluation of their effects on virus- and mock-infected cells. Five five-fold dilutions were made directly in the microtiter trays using a robot system. Untreated virus controls, and HeLa cell controls were included in each test. Approximately 100 TCID$_{50}$ of Respiratory Syncytial Virus was added to two of the three rows in a volume of 50 µl. The same volume of medium was added to the third row to measure the cytotoxicity of the compounds at the same concentrations as those used to measure the antiviral activity. After two hours of incubation, a suspension (4×10⁵ cells/ml) of HeLa cells was added to all wells in a volume of 50 μL. The cultures were incubated at 37° C. in a 5% $CO_2$ atmosphere. Seven days after infection the cytotoxicity and the antiviral activity was examined spectrophotometrically. To each well of the microtiter tray, 25 μL of a solution of MTT (3-(4,5-dimethylthiazol-2-yl)-2,5-diphenyltetrazolium bromide) was added. The trays were further incubated at 37° C. for 2 hours, after which the medium was removed from each cup. Solubilization of the formazan crystals was achieved by adding 100 μL 2-propanol. Complete dissolution of the formazan crystals was obtained after the trays were placed on a plate shaker for 10 min. Finally, the absorbances were read in an eight-channel computer-controlled photometer (Multiskan MCC, Flow Laboratories) at two wavelengths (540 and 690 nm). The absorbance measured at 690 nm was automatically subtracted from the absorbance at 540 nm, to eliminate the effects of non-specific absorption.

The invention claimed is:

1. A compound having the formula

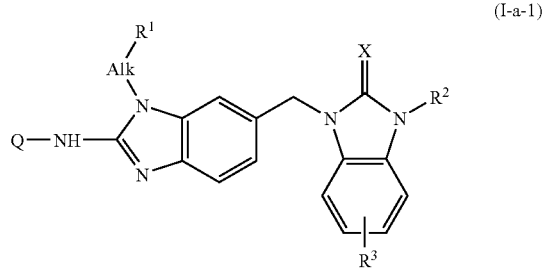

(I-a-1)

a salt or a stereochemically isomeric form thereof, wherein Q is $C_{1-6}$alkyl optionally substituted with a heterocycle or Q is $C_{1-6}$alkyl substituted with both a radical —$OR^4$ and a heterocycle; wherein said heterocycle is selected from the group consisting of oxazolidine, thiazolidine, 1-oxo-thiazolidine, 1,1-dioxothiazolidine, morpholinyl, thiomorpholinyl, 1-oxo-thiomorpholinyl, 1,1-dioxothiomorpholinyl, hexahydrooxazepine, hexahydrothiazepine, 1-oxo-hexahydrothiazepine, 1,1-dioxo-hexahydrothiazepine, pyrrolidine, piperidine, homopiperidine, piperazine; wherein each of said heterocyle may be optionally substituted with one or two substituents selected from the group consisting of $C_{1-6}$alkyl, hydroxy$C_{1-6}$alkyl, aminocarbonyl$C_{1-6}$alkyl, hydroxy, carboxyl, $C_{1-6}$alkyloxycarbonyl, aminocarbonyl, mono- or di($C_{1-6}$alkyl)-aminocarbonyl, $C_{1-6}$alkylcarbonylamino, aminosulfonyl and mono- or di($C_{1-6}$alkyl)aminosulfonyl;

Alk is $C_{1-6}$alkanediyl;

X is O or S;

$R^1$ is Ar or a heterocycle selected from pyridyl, pyrazinyl, pyridazinyl, pyrimidinyl, furanyl, tetrahydro-furanyl, thienyl, pyrrolyl, thiazolyl, oxazolyl, imidazolyl, isothiazolyl, pyrazolyl, isoxazolyl, oxadiazolyl, quinolinyl, quinoxalinyl, benzofuranyl, benzothienyl, benzimidazolyl, benzoxazolyl, benzothiazolyl, pyridopyridyl, naphthiridinyl, 1H-imidazo[4,5-b]pyridinyl, 3H-imidazo[4,5-b]-pyridinyl, imidazo[1,2-a]pyridinyl and 2,3-dihydro-1,4-dioxino[2,3-b]pyridyl; wherein each of said heterocycle may optionally be substituted with 1, 2, or 3 substituents each independently selected from the group consisting of halo, hydroxy, amino, cyano, carboxyl, $C_{1-6}$alkyl, $C_{1-6}$alkyloxy, hydroxy$C_{1-6}$ alkyloxy, ($C_{1-6}$alkyloxy)$C_{1-6}$alkyloxy, $C_{1-6}$alkylthio, $C_{1-6}$alkyloxy$C_{1-6}$alkyl, hydroxy$C_{1-6}$alkyl, mono- or di($C_{1-6}$alkyl)amino, mono- or di($C_{1-6}$alkyl)amino$C_{1-6}$ alkyl, polyhalo$C_{1-6}$alkyl, $C_{1-6}$alkylcarbonylamino, $C_{1-6}$alkyloxycarbonyl, aminocarbonyl, mono- and di-$C_{1-6}$alkylaminocarbonyl;

$R^2$ is hydrogen, $C_{1-6}$alkyl, hydroxy$C_{1-6}$alkyl, $C_{1-6}$alkyloxy$C_{1-6}$alkyl, Ar—$C_{1-6}$alkyloxy$C_{1-6}$alkyl, $C_{3-7}$cycloalkyl, cyano-$C_{1-6}$alkyl, Ar—$C_{1-6}$alkyl, Het-$C_{1-6}$alkyl;

$R^3$ is hydrogen, $C_{1-6}$alkyl, cyano, aminocarbonyl, polyhalo$C_{1-6}$alkyl, $C_{2-6}$alkenyl or $C_{2-6}$alkynyl;

$R^4$ is hydrogen or $C_{1-6}$alkyl;

each Ar independently is phenyl or phenyl substituted with 1 to 5, such as 1, 2, 3 or 4, substituents selected from halo, hydroxy, amino, mono- or di($C_{1-6}$alkyl)amino, $C_{1-6}$alkylcarbonylamino, $C_{1-6}$alkylsulfonylamino, cyano, $C_{1-6}$alkyl, $C_{2-6}$alkenyl, $C_{2-6}$alkynyl, phenyl, hydroxy$C_{1-6}$alkyl, polyhalo$C_{1-6}$alkyl, amino$C_{1-6}$alkyl, mono- or di($C_{1-6}$alkyl)amino$C_{1-6}$alkyl, $C_{1-6}$alkyloxy, polyhalo$C_{1-6}$alkyloxy, phenoxy, aminocarbonyl, mono- or di($C_{1-6}$alkyl)aminocarbonyl, hydroxycarbonyl, $C_{1-6}$alkoxycarbonyl, $C_{1-6}$alkylcarbonyl, aminosulfonyl, mono- and di($C_{1-6}$alkyl)aminosulfonyl;

Het is a heterocycle selected from the group consisting of pyridyl, pyrazinyl, pyridazinyl, pyrimidinyl, furanyl, tetrahydrofuranyl, thienyl, pyrrolyl, thiazolyl, oxazolyl, imidazolyl, isothiazolyl, pyrazolyl, isoxazolyl, oxadiazolyl, quinolinyl, quinoxalinyl, benzofuranyl, benzothienyl, benzimidazolyl, benzoxazolyl, benzothiazolyl, pyridopyridyl, naphthiridinyl, 1H-imidazo[4,5-b]pyridinyl, 3H-imidazo[4,5-b]pyridinyl, imidazo[1,2-a]pyridinyl and 2,3-dihydro-1,4-dioxino[2,3-b]pyridyl; wherein each Het may be optionally substituted with 1, 2 or 3 substituents each independently selected from halo, hydroxy, amino, mono- or di($C_{1-6}$alkyl)amino, cyano, $C_{1-6}$alkyl, hydroxy$C_{1-6}$alkyl, polyhalo$C_{1-6}$alkyl, $C_{1-6}$alkyloxy.

2. A compound according to claim 1 wherein $R^1$ is pyridyl substituted with 1 or 2 substituents independently selected from the group consisting of hydroxy, $C_{1-6}$alkyl, halo, $C_{1-6}$alkyloxy and ($C_{1-6}$alkyloxy)$C_{1-6}$alkyloxy.

3. A compound according to claim 1 wherein Alk is methylene.

4. A compound according to claim 1 wherein $R^2$ is $C_{1-6}$alkyl, hydroxy$C_{1-6}$alkyl, $C_{1-6}$alkyloxy$C_{1-6}$alkyl, $C_{3-7}$cycloalkyl, cyano-$C_{1-6}$alkyl.

5. A compound according to claim 1 wherein $R^3$ is hydrogen.

6. A compound according to claim 1 wherein $R^4$ is hydrogen.

7. A compound according to claim 1 wherein Q is $C_{1-6}$alkyl substituted with morpholinyl.

8. A pharmaceutical composition comprising a pharmaceutically acceptable carrier, and as active ingredient a therapeutically effective amount of a compound as claimed in claim 1.

9. A process for preparing a compound of formula (I-a-1), comprising reacting a benzimidazole derivative (II) with a reagent (III) to form the compound of formula (I-a-1)):

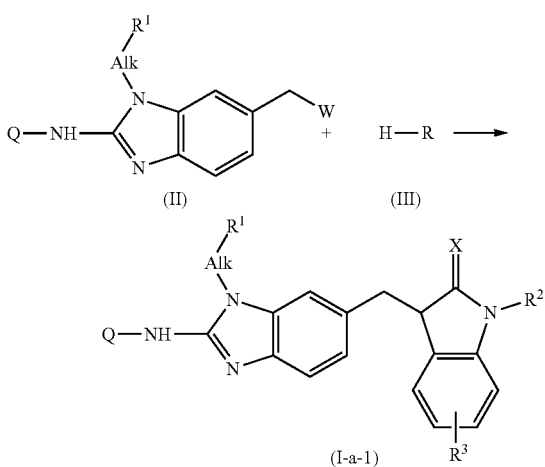

wherein Q is $C_{1-6}$alkyl optionally substituted with a heterocycle or Q is $C_{1-6}$alkyl substituted with both a radical —$OR^4$ and a heterocycle; wherein said heterocycle is selected from the group consisting of oxazolidine, thiazolidine, 1-oxo-thiazolidine, 1,1-dioxothiazolidine, morpholinyl, thiomorpholinyl, 1-oxo-thiomorpholinyl, 1,1-dioxothiomorpholinyl, hexahydrooxazepine, hexahydrothiazepine, 1-oxo-hexahydrothiazepine, 1,1-dioxo-hexahydrothiazepine, pyrrolidine, piperidine, homopiperidine, piperazine; wherein each of said heterocyle may be optionally substituted with one or two substituents selected from the group consisting of $C_{1-6}$alkyl, hydroxy$C_{1-6}$alkyl, aminocarbonyl$C_{1-6}$alkyl, hydroxy, carboxyl, $C_{1-6}$alkyloxycarbonyl, aminocarbonyl, mono- or di($C_{1-6}$alkyl)aminocarbonyl, $C_{1-6}$alkylcarbonylamino, aminosulfonyl and mono- or di($C_{1-6}$alkyl)aminosulfonyl, Alk is $C_{1-6}$alkanediyl, $R^1$ is Ar or a heterocycle selected from pyridyl, pyrazinyl, pyridazinyl, pyrimidinyl, furanyl, tetrahydro-furanyl, thienyl, pyrrolyl, thiazolyl, oxazolyl, imidazolyl, isothiazolyl, pyrazolyl, isoxazolyl, oxadiazolyl, quinolinyl, quinoxalinyl, benzofuranyl, benzothienyl, benzimidazolyl, benzoxazolyl, benzothiazolyl, pyridopyridyl, naphthiridinyl, 1H-imidazo[4,5-b]pyridinyl, 3H-imidazo[4,5-b]pyridinyl, imidazo[1,2-a]-pyridinyl and 2,3-dihydro-1,4-dioxino[2,3-b]pyridyl; wherein each of said heterocycle may optionally be substituted with 1, 2, or 3 substituents each independently selected from the group consisting of halo, hydroxy, amino, cyano, carboxyl, $C_{1-6}$alkyl, $C_{1-6}$alkyloxy, hydroxy$C_{1-6}$alkyloxy, ($C_{1-6}$alkyloxy)$C_{1-6}$alkyloxy, $C_{1-6}$alkylthio, $C_{1-6}$alkyloxy$C_{1-6}$alkyl, hydroxy$C_{1-6}$alkyl, mono- or di($C_{1-6}$alkyl)amino, mono- or di($C_{1-6}$alkyl)amino$C_{1-6}$alkyl, polyhalo$C_{1-6}$alkyl, $C_{1-6}$alkylcarbonylamino, $C_{1-6}$alkyloxycarbonyl, aminocarbonyl, mono- and di-$C_{1-6}$alkylaminocarbonyl, X is O or S;

$R^2$ is hydrogen, $C_{1-6}$alkyl, hydroxy$C_{1-6}$alkyl, $C_{1-6}$alkyloxy$C_{1-6}$alkyl, Ar—$C_{1-6}$alkyloxy$C_{1-6}$alkyl, $C_{3-7}$cycloalkyl, cyano-$C_{1-6}$alkyl, Ar—$C_{1-6}$alkyl, Het-$C_{1-6}$alkyl;

$R^3$ is hydrogen, $C_{1-6}$alkyl, cyano, aminocarbonyl, polyhalo$C_{1-6}$alkyl, $C_{2-6}$alkenyl or $C_{2-6}$alkynyl;

$R^4$ is hydrogen or $C_{1-6}$alkyl;

each Ar independently is phenyl or phenyl substituted with 1 to 5, such as 1, 2, 3 or 4, substituents selected from halo, hydroxy, amino, mono- or di($C_{1-6}$alkyl)amino, $C_{1-6}$alkylcarbonylamino, $C_{1-6}$alkylsulfonylamino, cyano, $C_{1-6}$alkyl, $C_{2-6}$alkenyl, $C_{2-6}$alkynyl, phenyl, hydroxy$C_{1-6}$alkyl, polyhalo$C_{1-6}$alkyl, amino$C_{1-6}$alkyl, mono- or di($C_{1-6}$alkyl)amino$C_{1-6}$alkyl, $C_{1-6}$alkyloxy, polyhalo$C_{1-6}$alkyloxy, phenoxy, aminocarbonyl, mono- or di($C_{1-6}$alkyl)aminocarbonyl, hydroxycarbonyl, $C_{1-6}$alkoxycarbonyl, $C_{1-6}$alkylcarbonyl, aminosulfonyl, mono- and di($C_{1-6}$alkyl)aminosulfonyl;

Het is a heterocycle selected from the group consisting of pyridyl, pyrazinyl, pyridazinyl, pyrimidinyl, furanyl, tetrahydrofuranyl, thienyl, pyrrolyl, thiazolyl, oxazolyl, imidazolyl, isothiazolyl, pyrazolyl, isoxazolyl, oxadiazolyl, quinolinyl, quinoxalinyl, benzofuranyl, benzothienyl, benzimidazolyl, benzoxazolyl, benzothiazolyl, pyridopyridyl, naphthiridinyl, 1H-imidazo[4,5-b]pyridinyl, 3H-imidazo[4,5-b]pyridinyl, imidazo[1,2-a] pyridinyl and 2,3-dihydro-1,4-dioxino[2,3-b]pyridyl; wherein each Het may be optionally substituted with 1, 2 or 3 substituents each independently selected from halo, hydroxy, amino, mono- or di($C_{1-6}$alkyl)amino, cyano, $C_{1-6}$alkyl, hydroxy$C_{1-6}$alkyl, polyhalo$C_{1-6}$alkyl, $C_{1-6}$alkyloxy; and W represents a leaving group; and optionally preparing a salt form of the compounds of formula (I) by reacting the base from with an appropriate acid or, where applicable, with a base.

10. A pharmaceutical composition made by mixing a compound of claim 1 and a pharmaceutically acceptable carrier.

11. A process for making a pharmaceutical composition comprising mixing a compound of claim 1 and a pharmaceutically acceptable carrier.

12. The pharmaceutical composition of claim 8, further comprising an antiviral agent.

13. The pharmaceutical composition of claim 12, further comprising an antiviral agent selected from the group consisting of interferon-beta and tumor necrosis factor-alpha.

* * * * *